(12) United States Patent
Chobotov

(10) Patent No.: US 11,752,021 B2
(45) Date of Patent: Sep. 12, 2023

(54) STENT GRAFT DELIVERY SYSTEM WITH ACCESS CONDUIT

(71) Applicant: TriVascular, Inc., Santa Rosa, CA (US)

(72) Inventor: Michael V. Chobotov, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 165 days.

(21) Appl. No.: 17/105,132

(22) Filed: Nov. 25, 2020

(65) Prior Publication Data

US 2021/0196493 A1 Jul. 1, 2021

Related U.S. Application Data

(63) Continuation of application No. 14/920,828, filed on Oct. 22, 2015, now Pat. No. 10,849,774.

(60) Provisional application No. 62/067,823, filed on Oct. 23, 2014.

(51) Int. Cl.
*A61F 2/966* (2013.01)
*A61F 2/07* (2013.01)
*A61F 2/954* (2013.01)
*A61F 2/06* (2013.01)

(52) U.S. Cl.
CPC ............... *A61F 2/966* (2013.01); *A61F 2/07* (2013.01); *A61F 2/954* (2013.01); *A61F 2002/061* (2013.01); *A61F 2002/067* (2013.01); *A61F 2002/077* (2013.01); *A61F 2250/0003* (2013.01)

(58) Field of Classification Search
CPC .. A61F 2/966; A61F 2/07; A61F 2/954; A61F 2002/061; A61F 2002/067; A61F 2250/0003
See application file for complete search history.

(56) References Cited

U.S. PATENT DOCUMENTS

| | | |
|---|---|---|
| 4,140,126 A | 2/1979 | Choudhury |
| 4,434,797 A | 3/1984 | Silander |
| 5,156,620 A | 10/1992 | Pigott |
| 5,176,659 A | 1/1993 | Mancini |
| 5,507,770 A | 4/1996 | Turk |
| 5,534,007 A | 7/1996 | Germain et al. |
| 5,662,703 A | 9/1997 | Yurek et al. |

(Continued)

FOREIGN PATENT DOCUMENTS

| | | |
|---|---|---|
| CN | 101094623 A | 12/2007 |
| CN | 101902988 A | 12/2010 |

(Continued)

OTHER PUBLICATIONS

Japanese Office Action dated Mar. 1, 2021, from application No. 2020-036501.

(Continued)

*Primary Examiner* — Richard G Louis

(74) *Attorney, Agent, or Firm* — Foley & Lardner LLP

(57) ABSTRACT

Embodiments discussed herein are directed to devices, systems and methods for effectively treating post endovascular procedure complications such as endoleaks within an aneurysm sac. Some embodiments may include a delivery system with an integral aneurysm sac conduit configured for the introduction of materials which may be useful for treating endoleaks or the like.

19 Claims, 15 Drawing Sheets

(56) References Cited

U.S. PATENT DOCUMENTS

| | | |
|---|---|---|
| 5,693,088 A | 12/1997 | Lazarus |
| 5,785,679 A | 7/1998 | Abolfathi et al. |
| 6,126,685 A | 10/2000 | Lenker et al. |
| 6,231,562 B1 | 5/2001 | Khosravi et al. |
| 6,395,019 B2 | 5/2002 | Chobotov |
| 6,443,941 B1 | 9/2002 | Slepian et al. |
| 6,463,317 B1 | 10/2002 | Kucharczyk et al. |
| 6,475,466 B1 | 11/2002 | Ricci et al. |
| 6,569,190 B2 | 5/2003 | Whalen, II et al. |
| 6,582,460 B1 | 6/2003 | Cryer |
| 6,730,119 B1 | 5/2004 | Smalling |
| 6,733,521 B2 | 5/2004 | Chobotov et al. |
| 6,939,374 B2 | 9/2005 | Banik et al. |
| 7,081,129 B2 | 7/2006 | Chobotov |
| 7,150,758 B2 | 12/2006 | Kari et al. |
| 7,255,711 B2 | 8/2007 | Holman et al. |
| 7,481,821 B2 | 1/2009 | Fogarty et al. |
| 7,530,988 B2 | 5/2009 | Evans et al. |
| 8,801,769 B2 | 8/2014 | Chobotov |
| 8,992,595 B2 | 3/2015 | Parsons et al. |
| 2001/0023369 A1 | 9/2001 | Chobotov |
| 2001/0041896 A1* | 11/2001 | Reiley ............... A61F 2/4601 606/93 |
| 2001/0047150 A1 | 11/2001 | Chobotov |
| 2001/0049509 A1 | 12/2001 | Sekine et al. |
| 2002/0019665 A1* | 2/2002 | Dehdashtian ............ A61F 2/07 623/1.13 |
| 2002/0155956 A1 | 10/2002 | Chamberlain et al. |
| 2003/0036727 A1* | 2/2003 | Schock ............... A61M 60/894 604/509 |
| 2003/0149395 A1* | 8/2003 | Zawacki ............ A61M 1/3653 604/40 |
| 2004/0044358 A1 | 3/2004 | Khosravi et al. |
| 2004/0098091 A1 | 5/2004 | Erbel et al. |
| 2005/0004660 A1 | 1/2005 | Rosenbluth et al. |
| 2005/0090804 A1 | 4/2005 | Chobotov et al. |
| 2006/0009833 A1 | 1/2006 | Chobotov et al. |
| 2006/0224232 A1 | 10/2006 | Chobotov |
| 2007/0078506 A1 | 4/2007 | McCormick et al. |
| 2007/0112413 A1 | 5/2007 | Smith |
| 2008/0058759 A1 | 3/2008 | Makower et al. |
| 2008/0255652 A1 | 10/2008 | Thomas et al. |
| 2009/0319029 A1 | 12/2009 | Evans et al. |
| 2011/0160833 A1 | 6/2011 | Gonzalez et al. |
| 2011/0218609 A1 | 9/2011 | Chobotov et al. |
| 2011/0230952 A1* | 9/2011 | Kassab ............ A61B 17/12118 623/1.13 |
| 2012/0016457 A1 | 1/2012 | Chobotov et al. |
| 2013/0268048 A1 | 10/2013 | Watson et al. |
| 2013/0338753 A1 | 12/2013 | Geusen |
| 2014/0088690 A1 | 3/2014 | Fogarty et al. |
| 2016/0022222 A1 | 1/2016 | Folk |

FOREIGN PATENT DOCUMENTS

| | | |
|---|---|---|
| CN | 101917929 A | 12/2010 |
| EP | 1683541 | 7/2006 |
| FR | 2834199 | 4/2003 |
| JP | 09-047513 | 2/1997 |
| JP | 2009-534112 A | 9/2009 |
| JP | 2011-518620 A | 6/2011 |
| WO | WO 98/041167 | 9/1998 |
| WO | WO-02/151336 A1 | 7/2002 |
| WO | WO 02/083038 | 10/2002 |
| WO | WO-03/103541 A1 | 12/2003 |
| WO | WO 04/037116 | 5/2004 |
| WO | WO 05/037076 | 4/2005 |
| WO | WO 06/107562 | 10/2006 |
| WO | WO 06/116725 | 11/2006 |
| WO | WO-2009/132309 A1 | 10/2009 |
| WO | WO 11/100367 | 8/2011 |
| WO | WO 11/158045 | 12/2011 |
| WO | WO 12/068175 | 5/2012 |
| WO | WO 16/065208 | 4/2016 |
| WO | WO 16/191602 | 12/2016 |
| WO | WO 17/019913 | 2/2017 |

OTHER PUBLICATIONS

Office Action dated Jul. 13, 2017 in U.S. Appl. No. 14/631,818, filed Feb. 25, 2015 and published as: US-2015/0164667 on: Jun. 18, 2015.

International Search Report and Written Opinion dated Feb. 2, 2016 in International Patent Application No. PCT/US2015/057016 filed, Oct. 22, 2015.

Non-Final Office Action dated Oct. 3, 2016 in U.S. Appl. No. 13/024,255, filed Feb. 9, 2011 and published as: 2011/0218609 on: Sep. 8, 2011.

Office Action Response dated Apr. 7, 2016 in U.S. Appl. No. 13/024,255, filed Feb. 9, 2011 and published as: 2011/0218609 on: Sep. 8, 2011.

Final Office Action dated Dec. 11, 2015 in U.S. Appl. No. 13/024,255, filed Feb. 9, 2011 and published as: 2011/0218609 on: Sep. 8, 2011.

Office Action Response dated Aug. 26, 2015 in U.S. Appl. No. 13/024,255, filed Feb. 9, 2011 and published as: 2011/0218609 on: Sep. 8, 2011.

Non-Final Office Action dated Mar. 26, 2015 in U.S. Appl. No. 13/024,255, filed Feb. 9, 2011 and published as: 2011/0218609 on: Sep. 8, 2011.

Notice of Allowance dated Jul. 29, 2016 in U.S. Appl. No. 13/835,491, filed Mar. 15, 2013 and published as: 2013/0268048 on : Oct. 10, 2013.

Office Action Response dated Feb. 16, 2016 in U.S. Appl. No. 13/835,491, filed Mar. 15, 2013 and published as: 2013/0268048 on : Oct. 10, 2013.

International Search Report and Written Opinion dated: Dec. 1, 2016 in International Patent Application No. PCT/US2016/044583 filed: Jul. 28, 2016 and published as: WO/2017/019913 on: Feb. 2, 2017.

Chinese Office Action dated Jul. 30, 2018, from application No. 201580057048.9.

Chinese Office Action dated Jun. 3, 2019, from application No. 201580057048.9.

Chinese Office Action dated Mar. 2, 2020, from application No. 201580057048.9.

European Office Action dated Jul. 3, 2019, from application No. 15852460.3.

Extended European Search Report dated May 15, 2018, from application No. 15852460.3.

Final Office Action dated Jun. 7, 2019, from U.S. Appl. No. 14/920,828.

Final Office Action dated Mar. 19, 2020, from U.S. Appl. No. 14/920,828.

International Search Report and Written Opinion dated Feb. 2, 2016, from application No. PCT/US2015/057016.

Japanese Office Action dated Sep. 4, 2019, from application No. 2017-521537.

Non-Final Office Action dated Dec. 9, 2019, from U.S. Appl. No. 14/920,828.

Non-Final Office Action dated Jan. 2, 2019, from U.S. Appl. No. 14/920,828.

Notice of Allowance dated Jul. 29, 2020, from U.S. Appl. No. 14/920,828.

Chinese Office Action dated Nov. 3, 2022, from application No. 202010827299.3.

* cited by examiner

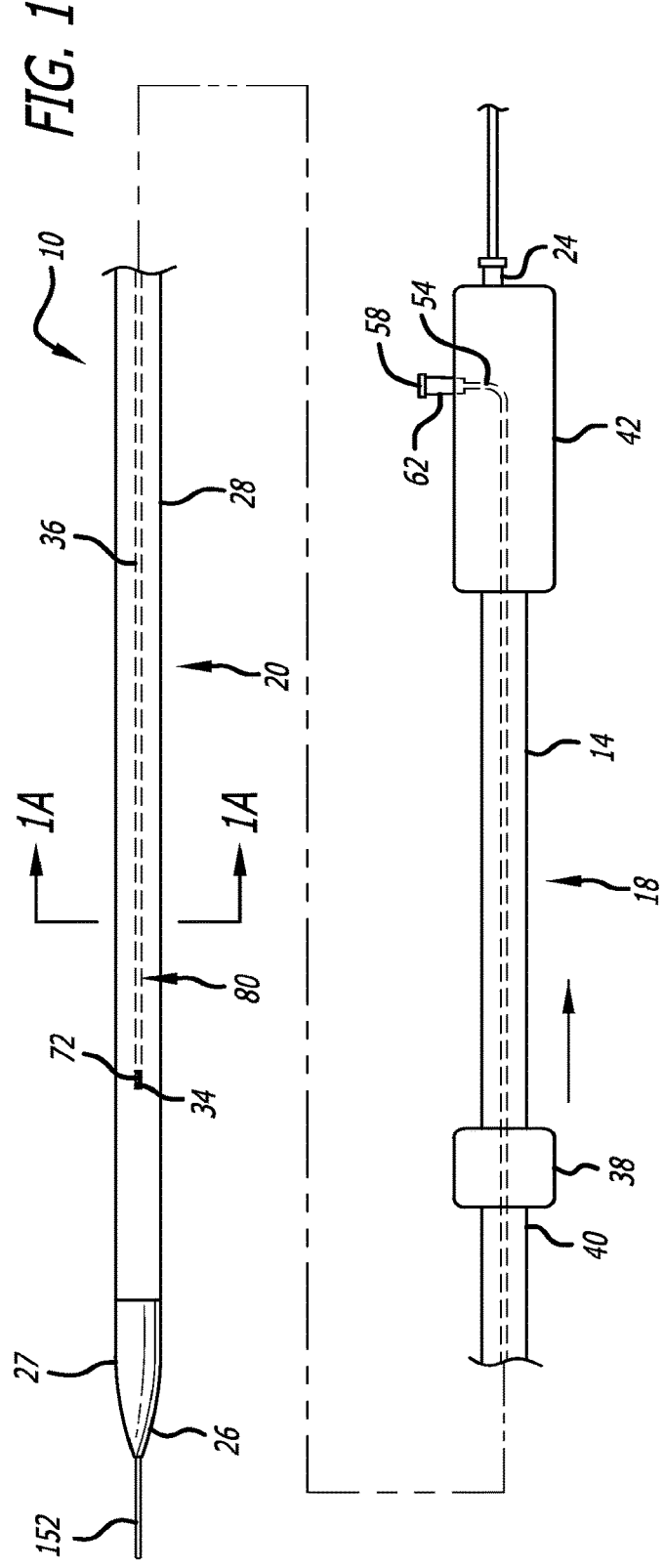

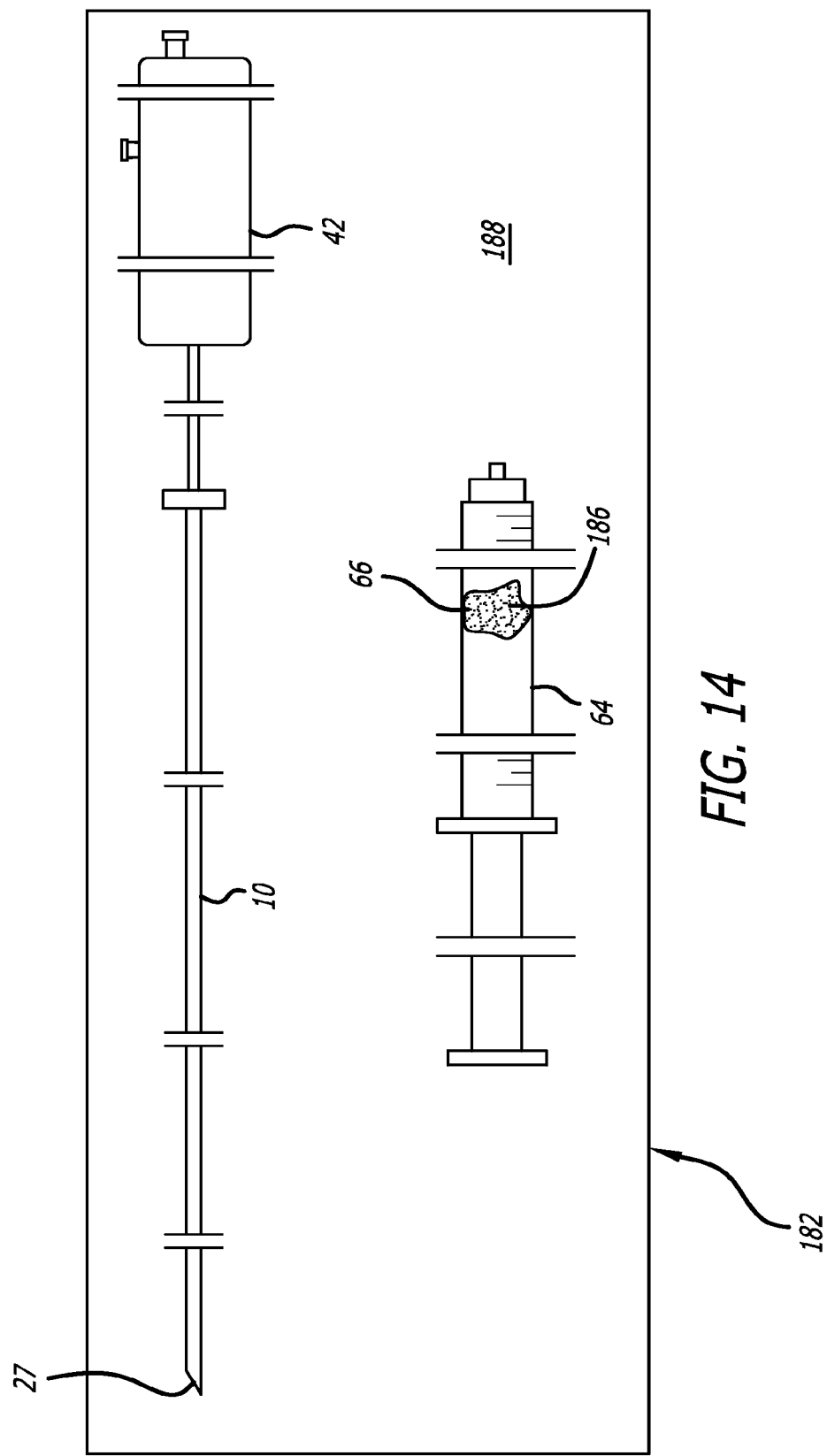

STENT GRAFT DELIVERY SYSTEM WITH ACCESS CONDUIT

RELATED PATENT APPLICATION(S)

This application is a continuation of U.S. patent application Ser. No. 14/920,828, filed Oct. 22, 2015, which claims priority under 35 U.S.C. 119(e) from U.S. Provisional Patent Application No. 62/067,823, filed Oct. 23, 2014, by Michael V. Chobotov, titled "Aneurysm Sac Access Conduit", which are incorporated by reference herein in their entirety.

BACKGROUND

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of an AAA is described in a book titled Surgical Treatment of Aortic Aneurysms by Denton A. Cooley, M.D., published in 1986 by W. B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W. L. Gore & Associates, Inc. of Newark, Del. A commercially available stent graft for the treatment of TAAs is the TAG™ system manufactured by W. L. Gore & Associates, Inc.

In some cases, follow-up of aneurysm repair, including endovascular repair of abdominal aortic aneurysms (EVAR), may be focused on assessing aneurysm exclusion by various imaging techniques, including duplex ultrasound, CT, angiography, MRI and the like. Persistent flow of blood into an aneurysm sac, also known as an endoleak, may precipitate the need to perform one or more additional subsequent interventions over time in order to mitigate a risk of aneurysm rupture due to continued sac pressurization from such an endoleak. In some cases, endoleaks may result in enlargement of the aneurysm sac over time. These endoleaks may also be difficult to isolate and occlude because the inflows and outflows relative to an inner volume of the aneurysm sac may be intermittent and small in scale, making the endoleaks difficult to image and access. What have been needed are devices, systems and methods for effectively treating post endovascular procedure complications such as endoleaks.

SUMMARY

Some embodiments of a delivery system for deployment of a stent graft may include a delivery catheter that has an elongate shaft with a proximal section and a distal section. The delivery catheter may also include a stent graft restraint that is configured to at least partially and releasably secure a stent graft in fixed relation to the elongate shaft. The delivery catheter may further include an elongate tubular access conduit extending from the proximal section to the distal section of the elongate shaft, the access conduit further including a proximal end, a distal end, a distal port, a proximal port and an inner lumen extending between and in fluid communication with the distal port and proximal port. A stent graft may be releasably secured to the distal section of the elongate shaft by the stent graft restraint with the stent graft in a radially constrained state. The stent graft itself may include a proximal end, a distal end, at least one inner lumen extending from the proximal end to the distal end, a proximal overlap section which extends distally from the proximal end of the stent graft and which has an axial length sufficient to couple and seal to an inner lumen, and a distal seal section which extends proximally from the distal end of the stent graft and which has an axial length sufficient to couple and seal to an inner surface of an inner lumen. In some cases, the stent graft may be positioned relative to the delivery catheter such that the distal end of the access conduit is disposed outside of an outer surface of the stent graft and axially positioned between a distal end of the proximal overlap section and a proximal end of the distal seal section of the stent graft.

Some embodiments of a method for treating an enlarged portion of a patient's body vessel may include advancing a delivery system through an inner lumen of the patient's body vessel. Such a delivery system may include a stent graft in a radially constrained state which may be releasably secured and positioned relative to a delivery catheter of the delivery system such that a distal end of an elongate tubular access conduit of the delivery catheter is disposed outside of an outer surface of the stent graft and the distal end of the access conduit is axially positioned between a distal end of a proximal overlap section, which extends distally from a proximal end of the stent graft, and a proximal end of a distal seal section, which extends proximally from a distal end of the stent graft. After so advancing the delivery system, at least a portion of a stent graft may be deployed such that the proximal overlap section of the stent graft is coupled and sealed to an inner lumen and a distal port of the access conduit is in fluid communication with an interior volume of the enlarged portion of the patient's body vessel.

Some embodiments of a kit for treating a defect of a patient's body lumen may include a delivery system for deployment of a stent graft. The delivery system may include a delivery catheter having an elongate shaft with a proximal section and a distal section, a stent graft restraint that is configured to at least partially and releasably secure a stent graft in fixed relation to the elongate shaft, and an elongate tubular access conduit. In some cases, the access conduit may extend from the proximal section to the distal section of the elongate shaft. For some embodiments, the access conduit may include a proximal end, a distal end, a distal port, a proximal port and an inner lumen extending between and in fluid communication with the distal port and proximal port. A stent graft may be releasably secured to the distal section of the delivery catheter by the stent graft restraint with the stent graft in a radially constrained state. The stent graft itself may include a proximal end, a distal end, at least one inner lumen extending from the proximal end to the distal end, a proximal overlap section which extends distally from the proximal end of the stent graft and which has an axial length sufficient to couple and seal to an inner lumen, a distal seal section which extends proximally from the distal end of the stent graft and which has an axial length sufficient to couple and seal to an inner surface of an inner lumen. In some instances, the stent graft may be positioned such that the distal end of the access conduit is disposed outside of an outer surface of the stent graft and axially positioned between a distal end of the proximal overlap section and a proximal end of the distal seal section of the stent graft. The kit may further include a thrombogenic agent for delivery through the inner lumen and from the distal port of the access conduit. In some cases, such a thrombogenic agent may be a liquid agent including materials such as Thrombin®, manufactured by GE Healthcare in Little Chalfont UK, Fibrin®, Floseal®, manufactured by Baxter Bioscience in Hayward Calif., Gelfoam®, manufactured by Pharmacia & Upjohn Company in Kalamazoo Mich., or the like. In some cases, the kit may also include a vessel or container, such as a syringe, which includes an internal volume to hold or otherwise contain the thrombogenic agent, the internal volume being capable of being pressurized in order to inject the thrombogenic agent through the inner lumen of the access conduit and into the defect of the patient's body lumen, such as an aneurysm.

Some embodiments of a method of detecting an endoleak during treatment of an aneurysm of patient may include advancing a delivery system through an inner lumen of an artery of the patient to the aneurysm or other similar treatment site. In some cases, such a delivery system may include a stent graft in a radially constrained state positioned relative to a delivery catheter of the delivery system such that a distal end of an elongate tubular access conduit of the delivery catheter is disposed outside of an outer surface of the stent graft. The stent graft may further be positioned such that the distal end of the access conduit is axially positioned between a distal end of a proximal overlap section, which extends distally from a proximal end of the stent graft, and a proximal end of a distal seal section, which extends proximally from a distal end of the stent graft. Once the delivery system has been so advanced, the stent graft may be deployed such that the aneurysm being treated is nominally isolated from the blood flow of the inner lumen of the artery and a distal port of the access conduit is in fluid communication with an interior volume of the aneurysm. The method may further include establishing an open fluid pathway between the interior volume of the aneurysm and a position outside the patient's body using an inner lumen of the access conduit. Once the open fluid pathway is established, the method may further include detecting ongoing blood leakage from a proximal port of the inner lumen of the access conduit. In some cases, detecting ongoing blood leakage may include detecting ongoing blood leakage using a fluid flowmeter which is coupled in fluid communication with the proximal port of the access conduit.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 1 is an elevation view of an embodiment of a stent graft delivery system.

FIG. 2 is an elevation view of the delivery system of FIG. 1 with an outer sheath thereof withdrawn in a proximal direction.

FIG. 14 is a top view of a kit embodiment that includes a delivery system and a substance for delivery through an access conduit of the delivery system.

DETAILED DESCRIPTION

As discussed above, after deployment of some stent graft systems in a patient's body vessel, certain types of blood flow into an aneurysm or other defect of a patient's body vessel being treated may persist. Residual flow of blood into an aneurysm sac, also known as an endoleak, may precipitate the need to perform one or more additional subsequent interventions over time in order to mitigate a risk of aneurysm rupture due to continued sac pressurization from such an endoleak. A technique that may be used both during initial implantation of a complete stent graft system that has nominally isolated an aneurysm, and in subsequent re-interventions with regard to a treated aneurysm, in order to treat endoleaks may include accessing the aneurysm sac with a small bore catheter and injecting thrombogenic material or some other suitable bioactive or clinically useful agent 66 into an interior volume of the aneurysm sac. Such materials including Thrombin®, Fibrin®, Floseal®, Gelfoam®, contrast agent, saline solution etc. or mixtures thereof may be useful to promote clotting within the aneurysm sac and arresting endoleaks including type 1 and type 2 endoleaks. Type 1 endoleaks typically include endoleaks in which flow enters the sac at the proximal and/or distal margins of a stent graft. Type 2 endoleaks may include leaks into an aneurysm sac due to flow reversal of blood through arteries in communication with the interior volume of the aneurysm which have not been directly shunted or treated. For example, patent lumbar or inferior mesenteric arteries may provide a conduit for flow of blood into an abdominal aortic aneurysm (which has been otherwise isolated by a deployed stent graft system) due to flow reversal of blood through those arteries.

Although such post stent graft deployment treatment may be possible, it may be difficult or impractical in many circumstances due to the difficulty in accessing the interior volume of the aneurysm sac once a stent graft system has been completely deployed. In particular, accessing the interior volume of the aneurysm sac after deployment of a complete stent graft system which has nominally isolated the aneurysm may be challenging since the distal ends of the stent graft(s) are typically in intimate apposition to the artery walls in landing/sealing zones such as in inner surface of a patient's aorta and iliac arteries. The intimate apposition of the stent graft(s) presents a difficult pathway for passage of a guidewire or the like which must be forced between the stent graft and artery wall in order to provide a guide mechanism over which a tubular access catheter may pass.

Figure 1A:
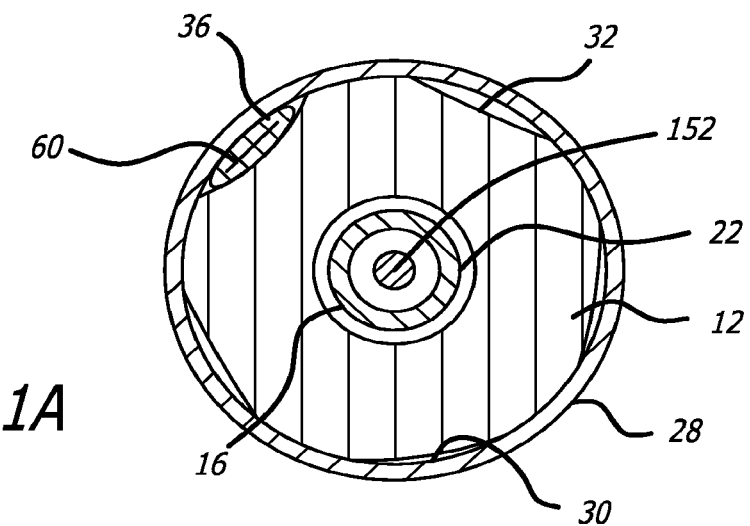
FIG. 1A is an enlarged cross section view of the delivery system of FIG. 1 taken along lines 1A-1A showing a thin walled collapsible access conduit embodiment.
Figure 1B:
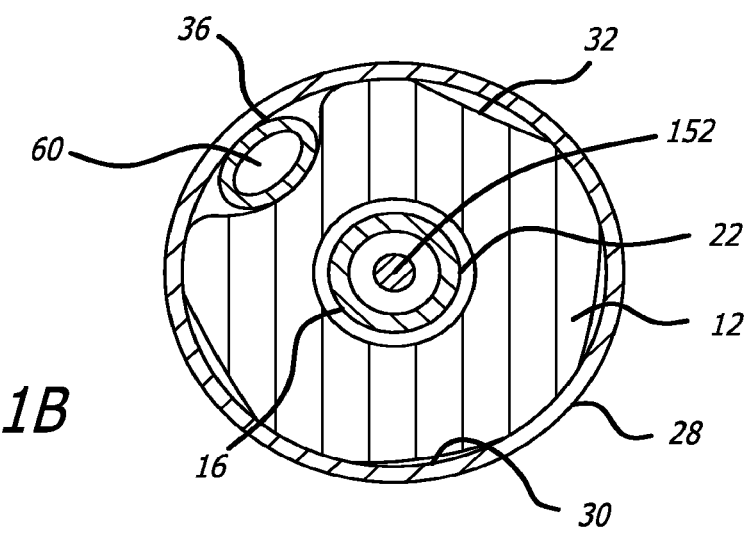
FIG. 1B is an enlarged cross section view of the delivery system of FIG. 1 similar to FIG. 1A showing a non-collapsible access conduit embodiment.
Figure 2A:
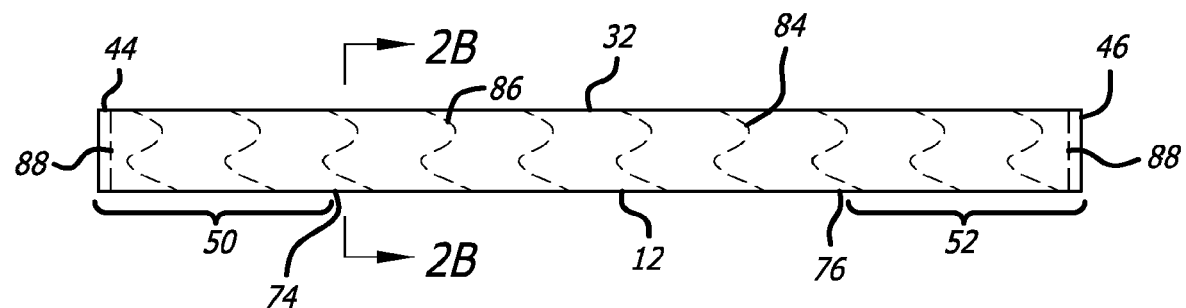
FIG. 2A is an elevation view of a tubular stent graft embodiment suitable for use with the delivery system embodiment shown in FIGS. 1 and 2 and shown in a relaxed, self-expanded state.
Figure 2B:
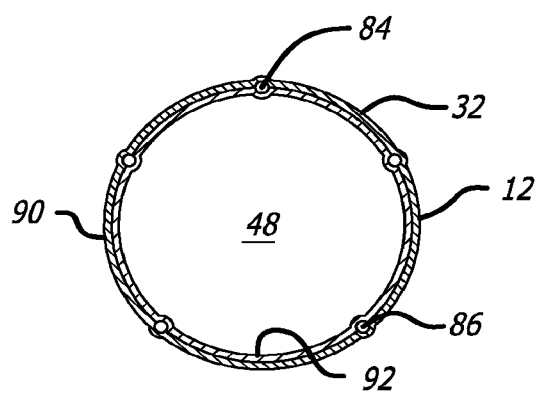
FIG. 2B is a cross section view taken along lines 3-3 of the stent graft embodiment in FIG. 2A.

To facilitate access to the aneurysm sac during and after stent graft deployment, the delivery catheter of a delivery system for deployment of a stent graft or stent graft component such as the final component of a modular AAA stent graft system (e.g. iliac limb stent graft) may be configured to reliably and effectively provide a fluid conduit pathway into an interior volume of an aneurysm sac or the like during or after deployment of a stent graft that spans the aneurysm. Referring to FIGS. 1-2B, some embodiments of a delivery system 10 for deployment of a stent graft 12 may include a delivery catheter 14 that has an elongate shaft 16 with a proximal section 18 and a distal section 20. The elongate shaft 16 of the delivery catheter 14 optionally includes an elongate tubular guidewire lumen 22 extending from a proximal end 24 of the elongate shaft 16 to a distal end 26 of the elongate shaft 16. The delivery catheter 14 may also include an optional bullet shaped nosecone 27 disposed at the distal end 26 of the elongate shaft 16. For some embodiments, including percutaneous systems, the elongate shaft 16 of the delivery catheter 14 may have an axial length of about 100 cm to about 300 cm.

The delivery catheter 14 may also include a stent graft restraint that is configured to at least partially and releasably secure a stent graft 12 in fixed relation to the elongate shaft 16. For the embodiment shown, the stent graft 12 restraint includes an axially slidable outer sheath 28 disposed over the stent graft and elongate shaft 16 with an inner surface 30 of a distal section of the outer sheath 28 being configured to radially constrain the outer surface 32 of the stent graft 12 and with a distal end 34 of an access conduit 36 being disposed between the outer surface 32 of the stent graft 12 and the inner surface 30 of the outer sheath 28 when the outer sheath 28 is disposed in a distal-most axial position. The outer sheath 28 may be proximally retracted by pulling proximally on a proximal grip 38 disposed at a proximal end 40 of the outer sheath 28. The delivery catheter 14 may also include a proximal handle/adapter 42 at proximal end 24 of the elongate shaft 16 as shown in FIG. 1.

The stent graft 12 may be at least partially releasably secured to the distal section 20 of the elongate shaft 16 by the stent graft restraint, which includes the outer sheath 28 for the embodiment shown, with the stent graft 12 in a radially constrained state. The stent graft 12 itself may include a proximal end 44, a distal end 46, at least one inner lumen 48 extending from the proximal end 44 to the distal end 46 (see also FIGS. 2A-2B). The stent graft 12 also includes a proximal overlap section 50 which extends distally from the proximal end 44 of the stent graft 12 and which has an axial length sufficient to couple and seal to an inner lumen, and a distal seal section 52 which extends proximally from the distal end 46 of the stent graft 12 and which has an axial length sufficient to couple and seal to an inner surface of an inner lumen. In some instances, the proximal overlap section 50 may have an axial length sufficient to couple and seal to an inner surface of an inner lumen of an endoluminal prosthesis and the distal seal section 52 may have an axial length sufficient to couple and seal to an inner surface of a patient's vessel. In some cases, the proximal overlap section 50 of the stent graft 12 may have an axial length of about 1 cm to about 5 cm and the distal seal section 52 of the stent graft 12 may have an axial length of about 1 cm to about 10 cm. For some embodiments, the stent graft 12 may be configured as a self-expanding stent graft 12. For some embodiments, the stent graft 12 may be configured as a tubular stent graft 12 having a single inner lumen 48 extending the longitudinal length thereof and having an inner transverse dimension of about 5 mm to about 30 mm. In some cases, the stent graft 12 may have an axial length of about 5 cm to about 20 cm.

The elongate tubular access conduit 36 extends from the proximal section 18 of the elongate shaft 16 to the distal section 20 of the elongate shaft 16. In some cases, such an access conduit 36 may be an integral part of a stent graft delivery system 10 or delivery catheter 14 thereof. The access conduit 36 includes a proximal end 54, the distal end 34, a distal port 56, a proximal port 58 and an inner lumen 60 extending between and in fluid communication with the distal port 56 and proximal port 58. In some cases, the proximal port 58 of the access conduit 36 may be disposed on the proximal handle 42 of the delivery catheter 14 and may include a luer fitting 62 for attachment of a syringe 64 containing the thrombogenic material or other suitable clinically useful material 66 to be injected through the access conduit 36 and into an interior volume 68 of an aneurysm 70. In some cases, a plurality of distal ports may be disposed at or near the distal end 34 of the access conduit 36 in order to diffuse a flow of material being emitted and reduce a force of a jet of such fluid or material. For some embodiments, up to 10 distal port orifices may be disposed at or near the distal end 34 of the access conduit 36. In some instances, the tubular structure of the access conduit 36 may have a nominal wall thickness of about 0.0005 inches to about 0.003 inches.

A radiopaque marker 72 may be disposed on the access conduit 36 at or near the distal end 34 of the access conduit 36. In some cases, the radiopaque marker 72 may include a heavy metal having an atomic number of at least about 70, including gold, platinum, tantalum etc. In some cases, the radiopaque marker 72 may include a powdered heavy metal such as bismuth or tantalum.

For the embodiment shown, the stent graft 12 and access conduit 36 may be positioned relative to each other such that the distal end 34 of the access conduit 36 is disposed outside of the abluminal/outer surface 32 of the stent graft 12 and axially positioned between a distal end 74 of the proximal overlap section 50 and a proximal end 76 of the distal seal section 52 of the stent graft 12. The proximal port 58 may be in fluid communication with the inner lumen 60 of the tubular access conduit 36 inside the outer sheath 28 of the delivery system 10, and may be configured during initial delivery system 10 assembly and loading to run along an outer/ablumenal surface 32 of the stent graft 12 with the stent graft 12 in a collapsed radially constrained state as shown in FIGS. 1A and 2. The distal end 34 of the access conduit 36 may also be disposed by a predetermined axial distance from the proximal end 44 of the stent graft 12 as indicated by arrow 75 in FIG. 2. For purposes of the discussion herein, the proximal end of the stent grafts and stent graft components is defined as the end disposed towards the source of blood flow within the patient's vasculature, i.e., the upstream end. The proximal end of the delivery systems, delivery system components and access conduit embodiments is the end closest the operator of the respective device.

Embodiments of the access conduit 36 may be constructed from one or more of a variety of materials, including various metals, polytetrafluoroethylene (PTFE), polyethylene terathalate (PET), Mylar®, polyurethane, etc. and may be rigid or semi-rigid. In particular, for some embodiments, the access conduit 36 may be a rigid self-supporting tube. In addition, some embodiments of the access conduit 36 may be made of a soft supple material with a thin walled tubular construction so as to be collapsible to reduce a cross section profile of the access conduit 36 and reduce a cross section area impact to the cross section area and outer transverse dimension of a delivery system 10 embodiment that incorporates such an access conduit 36. Such a soft and thin walled configuration of access conduit 36 may also reduce the risk of leakage out of the aneurysm sac 70 at the interface between the access conduit 36 and the distal edge of a deployed stent graft component.

For some embodiments, the access conduit 36 may optionally be axially slidably and/or rotationally movable with respect to an elongate shaft 16 of the delivery system 10 such that the access conduit 36 may be axially advanced, axially retracted and rotated about a longitudinal axis 77 thereof as needed to position a distal end 34 of the access conduit 36 optimally within the aneurysm sac 70. The access conduit 36 may also have a preformed resilient curve or other shape 78 at a distal section 80 of the access conduit 36, as indicated by the dashed line profile of the distal section 80 of the access conduit 36 in FIG. 2, to facilitate optimal placement of a distal end 34 and/or distal port 56 of the access conduit 36 within an interior volume 68 of an enlarged portion of the patient's vessel (such as the aneurysm 70) during use.

Figure 3:
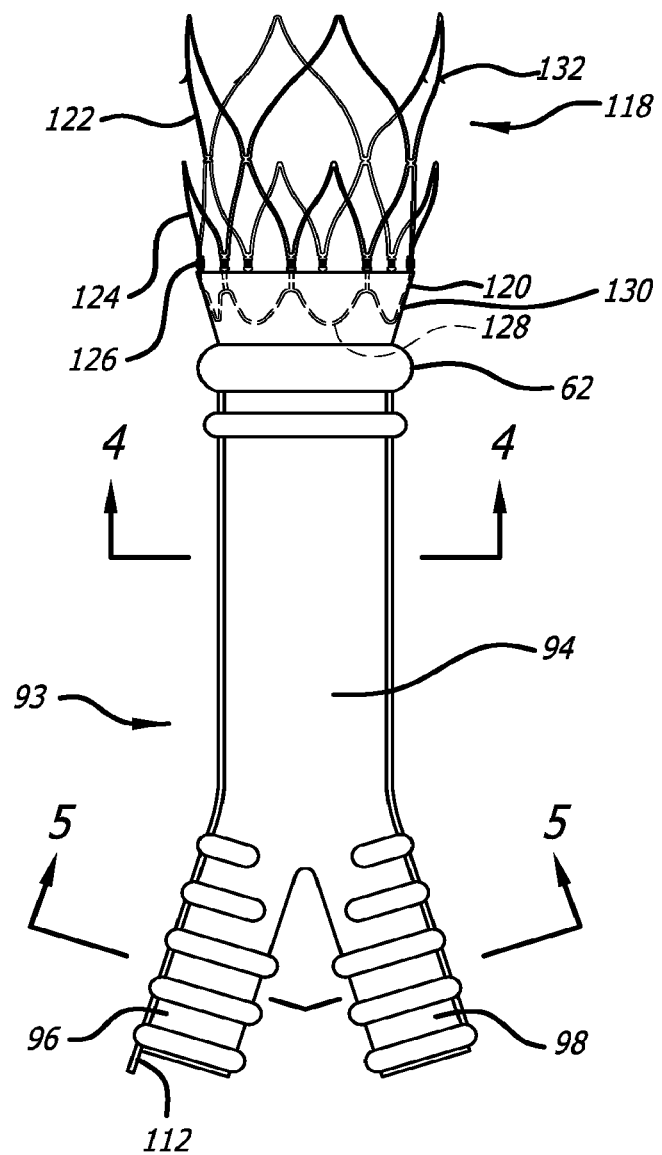
FIG. 3 is an elevation view of an embodiment of an inflatable stent graft.
Figure 4:
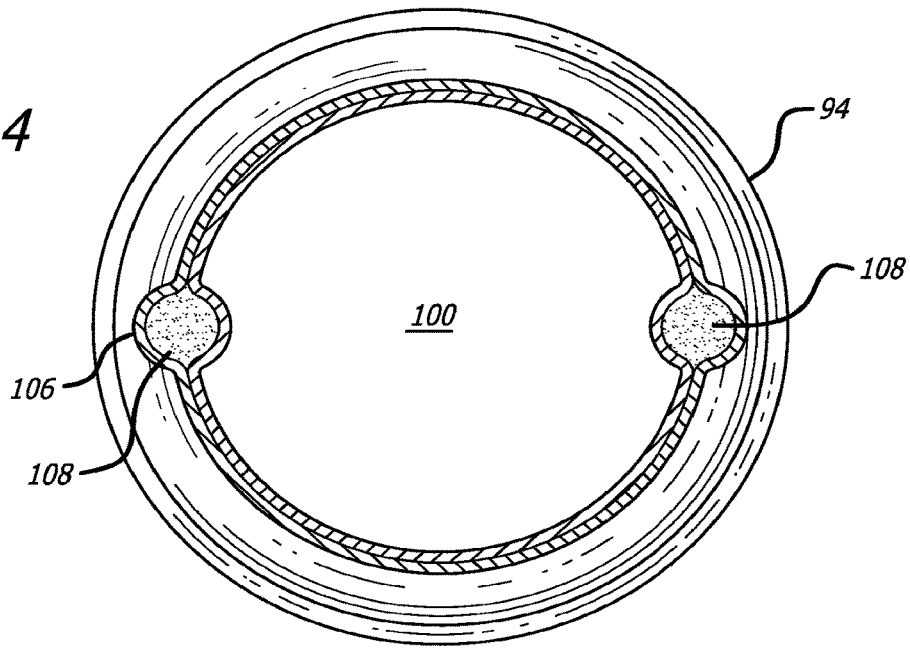
FIG. 4 is a transverse cross section view of the stent graft of FIG. 3 taken along lines 4-4 of FIG. 3.
Figure 5:
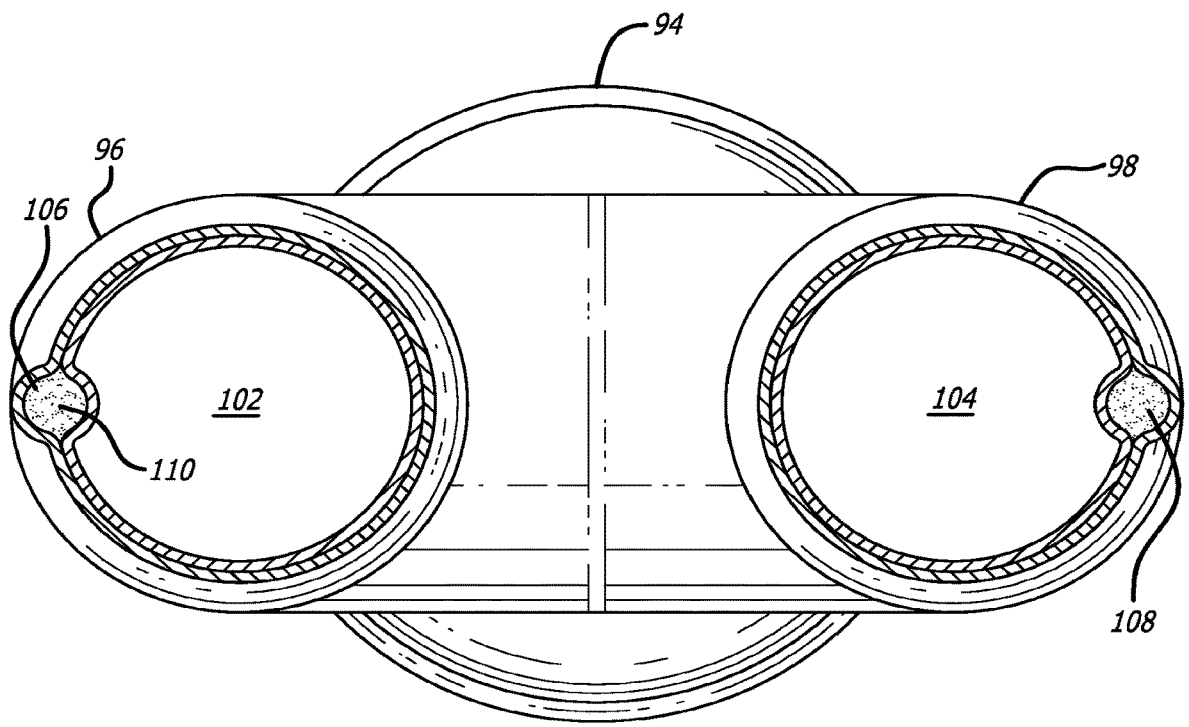
FIG. 5 is a transverse cross section view of the stent graft of FIG. 3 taken along lines 5-5 of FIG. 3.

As discussed above, delivery systems 10 that include an access conduit 36 useful for treating endoleaks as discussed herein may be used to deploy a wide variety of stent graft configurations. In some cases, such delivery systems 10 may be used to delivery components of a multi-component or modular stent graft system. Examples of components of such a modular and bifurcated stent graft system are shown in FIGS. 2A-5. The stent graft embodiments shown include a tubular extension stent graft 12 (FIGS. 2A-2B) and an embodiment of a bifurcated and optionally inflatable main body portion of an endoluminal prosthesis/stent graft for treatment of an abdominal aortic aneurysm 70 of a patient (FIGS. 3-5). More detail regarding some of these stent graft embodiments is provided below.

A delivery system for a two piece modular AAA stent graft system may include an integral access conduit 36 within either or both of its delivery catheters of the respective delivery systems for each of the two stent graft pieces, since access to the aneurysm sac 70 may be achieved from either the ipsilateral or contralateral sides. A delivery system for a three piece modular AAA stent graft system may also include such an integral access conduit 36 within either or both iliac limb stent graft delivery systems rather than the delivery system of the aortic body, since the delivery system for the latter may be removed prior to completion of the stent graft system/device being deployed.

Stent grafts, such as stent graft extension 12 may include a PTFE covered helical nitinol (nickel titanium alloy/NiTi) stent 84 with layers of PTFE, Dacron® or other suitable flexible layer material having a variety of characteristics. Regarding the stent 84 of the stent graft embodiment 12 of FIGS. 2A-2B, it may be formed from an elongate resilient stent element 86 which is helically wound with a plurality of longitudinally spaced turns. Some stent embodiments 84 may be generally helical in configuration with serpentine or other regularly space undulations transverse to the helical path of the elongate stent element 86 as shown in more detail in FIG. 2A. The ends of the stent element 86 may be secured to adjacent ring portions 88 of the stent as shown to avoid exposure of element ends to either PTFE graft material or possible patient tissues. The stent element 86 of the stent 84 shown in FIG. 2A is a continuous element from one end of the extension 12 to the other end thereof. The ends of the elongate element 86 may be secured to adjacent ring members 88 by any suitable means such as adhesive bonding, welding such as laser welding, soldering or the like. For some embodiments, the stent element 86 may have a transverse dimension or diameter of about 0.005 inch to about 0.015 inch.

For some embodiments of stent graft 12, layers of materials having different properties may be used in combination to achieve a desired clinical performance. For example, some layers of PTFE covering the stent may be permeable, semi-permeable or substantially non-permeable depending on the desired performance and material properties. FIG. 2B illustrates a transverse cross sectional view of an embodiment of stent graft extension 12 of FIG. 2A that shows an outer layer 90 which may include PTFE and an inner layer 92 which may also include PTFE. The layers 90, 92 may be applied by a variety of methods and have a variety of configurations. For example, some layer embodiments 90, 92 may include extruded tubular structures applied axially over a mandrel or subassembly. Some layer embodiments 90, 92 may be applied by wrapping layers circumferentially or wrapping tapes or ribbons in an overlapping helical pattern. For some embodiments, the outer layer 90 may be made from or include a semi-permeable or substantially non-permeable PTFE layer and the inner layer 92 may be made of or include a permeable layer of PTFE. The material of the inner and outer layers 90, 92 of the stent graft 12 shown may have a thickness for some embodiments of about 0.00005 inch to about 0.005 inch.

Figure 8:
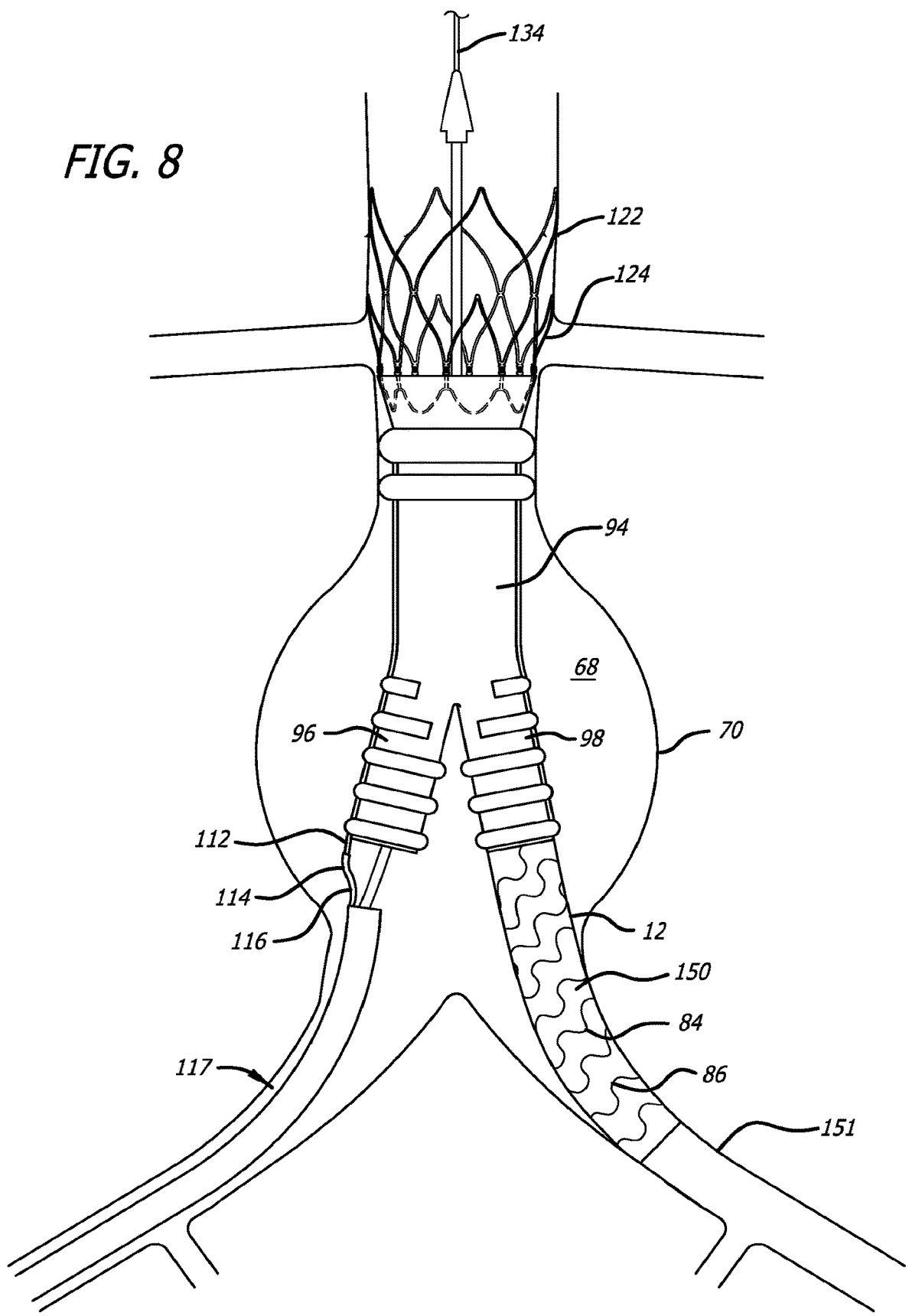
FIG. 8 illustrates the stent graft of FIG. 7 with a contralateral stent graft extension coupled to a contralateral leg of the stent graft and iliac artery of the patient's vasculature.

Referring to FIGS. 3-5, an inflatable bifurcated endoluminal prosthesis or stent graft 93 is shown having a main graft member or body portion 94, an ipsilateral leg 96 and contralateral leg 98. The main graft body 94 portion may have a substantially tubular configuration and has a wall portion that bounds a main fluid flow lumen 100 disposed therein. The ipsilateral leg 96 which may be of a substantially tubular configuration has an ipsilateral port and an ipsilateral fluid flow lumen 102 that is in fluid communication with the main fluid flow lumen 100 and the ipsilateral port. The contralateral leg 98, which may be of a substantially tubular configuration, has a contralateral port and a contralateral fluid flow lumen 104 that is in fluid communication with the main fluid flow lumen 100 and the contralateral port. The main graft portion 94, ipsilateral leg 96 and contralateral leg 98 form a graft portion having a bifurcated "Y" shaped configuration. The main body portion 94 and legs 96, 98 of the stent graft 93 may include and be formed from at least one flexible layer of material such as PTFE, polymer meshes, composites of same or the like. For some embodiments, the main body portion 94, ipsilateral leg 96 and contralateral leg 98 may include or be made from about 2 layers to about 15 layers or more of PTFE, polymer meshes, composites of the same or any other suitable material. The stent graft embodiment 93 is shown for purposes of illustration with an optional inflatable portion 106 thereof in an inflated state with the inflatable portion 106 full of a fill material 108. The optional inflatable portion 106 of the stent graft 93 shown includes an interior volume 110 which may be in fluid communication with an inflation port 112, and a distal end 114 of a fill tube 116 of the delivery catheter 117 releasably coupled to the inflation port 112 as shown in FIG. 8.

The main fluid flow lumen 100, shown in FIG. 4, of the main graft portion 94 generally may have a larger transverse dimension and area than a transverse dimension and area of either of the fluid flow lumens of the ipsilateral leg 96 or contralateral leg 98, respectively. A proximal anchor member or stent 118 is disposed at a proximal end 120 of the main graft portion 94 and may have a substantially cylindrical or tubular configuration for some embodiments. The proximal anchor member 118 embodiment shown in FIG. 3 includes a dual stent configuration including a first self-expanding stent member 122 disposed at a proximal position of the stent graft 93. The first self-expanding stent member 122 is formed from an elongate element having a generally serpentine shape with four crowns or apices at either end. Each distal apex or crown of the first self-expanding stent member 122 is coupled to alternating proximal crowns or apices of a second self-expanding stent member 124. The second self-expanding stent member 124 is disposed distally of the first self-expanding stent member 122 and is formed from an elongate element having a generally serpentine shape. A distal end 126 of the second self-expanding stent member 124 may be mechanically coupled to a connector ring 128 which is embedded in graft material of the proximal end 120 of the main graft portion 94, or directly coupled to perforations in a proximal edge region 130 of the main graft 94.

Some embodiments of the first self-expanding stent member 122 may include outwardly extending barbs 132. Such barbs 132 may be integrally formed with the struts of the self-expanding stent member, having sharp tissue penetrating tips that may be configured to penetrate into tissue of an inside surface of a lumen within which the proximal stent is deployed in an expanded state. Although the proximal anchor member 118 is shown as including first and second self-expanding stent members 122, 124, the proximal anchor member 118 may include similar stents that are configured to be inelastically expanded with outward radial pressure as might be generated by the expansion of an expandable balloon from within either or both of the first and second stents. As such, where practical, a balloon expandable type stent may be substituted for any self-expanding stent discussed herein. Such balloon expandable stent embodiments may have many or most of the same or similar features, dimensions and materials as compatible self-expanding stent embodiments. The connector ring 128 coupled to the second self-expanding stent member 124 may also be inelastically expandable for some embodiments. The self-expanding proximal anchor member embodiments, including each of the first and second self-expanding stent members 122, 124, may be made from or include a superelastic alloy, such as NiTi alloy.

Figure 6:
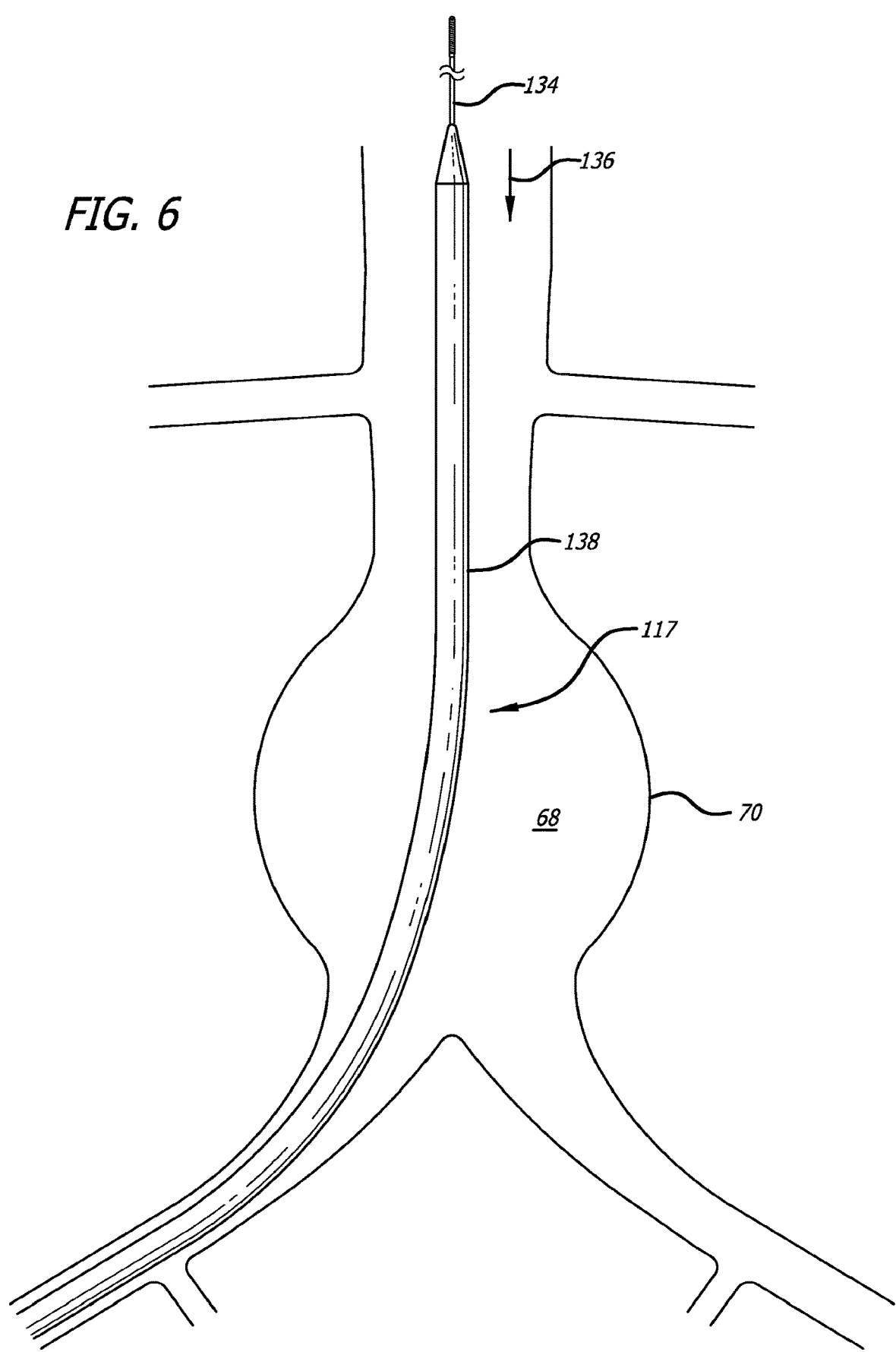
FIG. 6 illustrates a delivery system embodiment disposed over a guidewire embodiment within a patient's abdominal aorta and crossing an abdominal aortic aneurysm.
Figure 7:
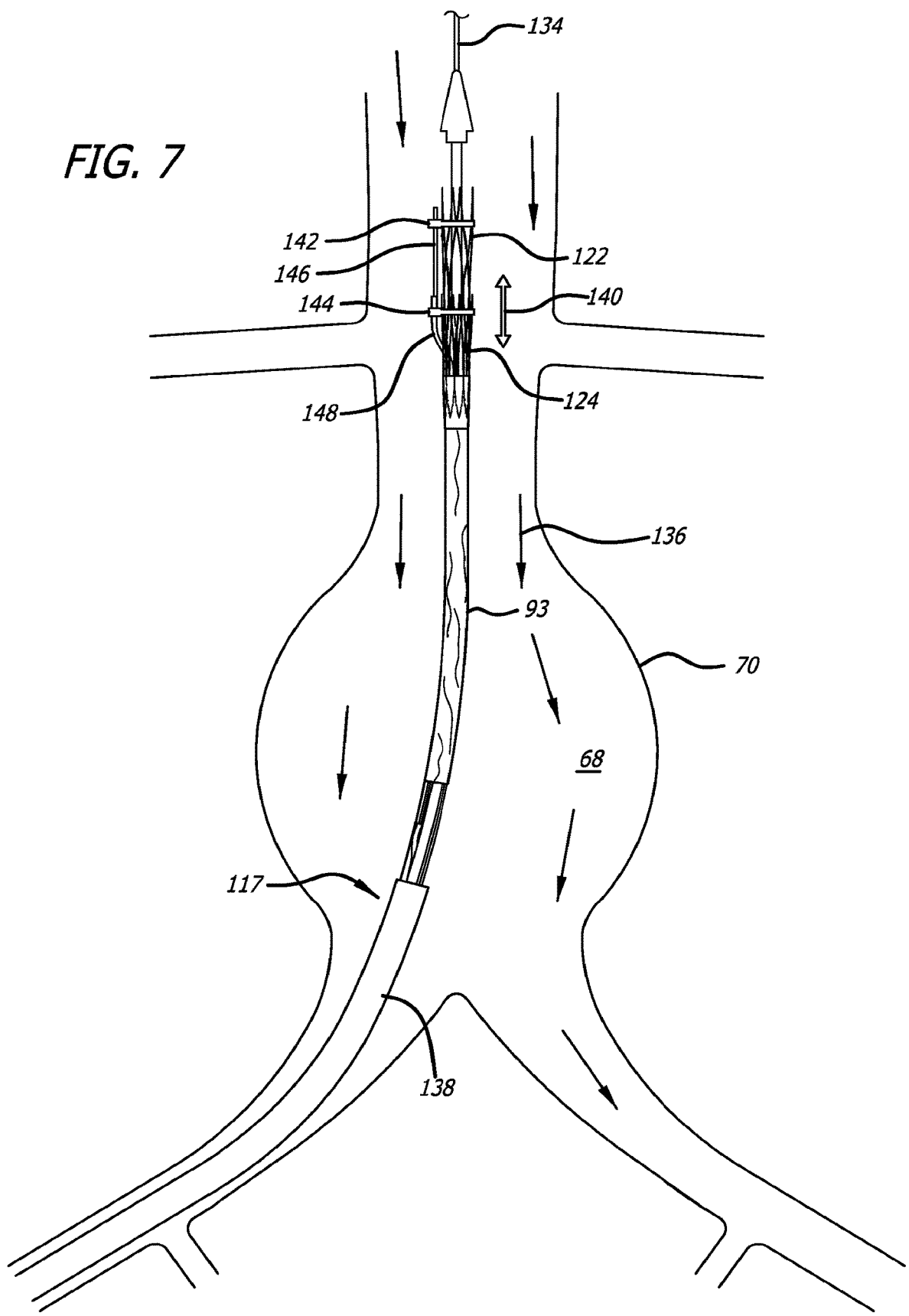
FIG. 7 illustrates the delivery system of FIG. 6 with an outer sheath of the delivery system retracted distally.

In some circumstances, an endoluminal prosthesis such as the bifurcated endoluminal prosthesis 93 shown in FIGS. 3-5 may be deployed in a patient's vessel prior to use of a delivery system 10 that includes an integral access conduit 36. For some embodiments, the delivery system 117 used to deploy such a bifurcated endoluminal prosthesis 93 may also optionally include an integral access conduit 36 (not shown) for some indications. FIGS. 6-8 illustrate deployment of the bifurcated inflatable stent graft 93, shown in FIGS. 3-5. The positioning and deployment method embodiments illustrated in FIGS. 6-8 and discussed herein, may be used to deploy a variety of stent graft embodiments, optionally including inflatable stent graft embodiments, non-inflatable stent graft embodiments, tubular single lumen stent graft embodiments, such as is shown in FIGS. 2A and 2B, and the like. Such stent graft embodiments may be deployed in a desired position of a patient's vasculature and in a desired orientation with respect to a patient's vasculature. The illustrated methods may be useful in maintaining control of the deployment process and allow treating personnel to accurately place the endoluminal prosthesis while minimizing stresses on the endoluminal prosthesis and the patient's vasculature.

Referring to FIG. 6, the delivery catheter 117 containing the bifurcated endoluminal prosthesis/stent graft 93 in a radially constrained state is advanced to a deployment site within a patient's vasculature. The delivery catheter 117 may be advanced over a guidewire 134 such that a proximal end 120 of the stent graft 93 is disposed towards a flow of blood, as indicated by arrow 136, within the patient's vasculature. The constrained stent graft 93, which is disposed beneath an outer sheath 138 of the delivery catheter 117, may be axially positioned within the patient's vasculature (as indicated by arrow 140) adjacent a treatment site as shown in FIG. 7. The treatment site embodiment shown includes an abdominal aortic aneurysm 70 within a patient's vasculature.

Once the delivery catheter 117 has been disposed at a desired treatment site 70, the outer sheath 138 of the delivery catheter 117 may be retracted distally as shown in FIG. 7. Once the outer sheath 138 of the delivery catheter 117 is retracted, the stent graft 93 which is releasably secured to the delivery catheter 117 with the proximal anchor member 118 in a constrained state is exposed. For some embodiments, retraction of the outer sheath 138 from the stent graft 93 may put the stent graft 93 in a partially deployed state. At this stage, the proximal anchor member 118 of the stent graft 93 may still be restrained by an optional first belt member 142 and an optional second belt member 144 disposed about the first self-expanding stent member 122 and second self-expanding stent member 124 of the proximal anchor member 118 respectively. Looped ends of the first belt member 142 may be releasably secured together with a first release wire 146 which passes through the looped ends of the first belt member 142. Looped ends of the second belt member 144 may be releasably secured together with a second release wire 148 which passes through the looped ends of the second belt member 144. The distal or second belt member 144 may be released by retraction in a proximal direction of the second release wire 148 so as to remove the circumferential constraint of the second belt member 144 about the second stent member 24 of the proximal anchor member 118. Removal of the circumferential constraint of the second belt member 144 may be used to partially or fully deploy the stent graft 93. Such belts 142, 144 may also be used as stent graft restraints for delivery system embodiments 10 that include access conduits 36 for endoleak management.

For the modular bifurcated endoluminal prosthesis/stent graft component embodiment 93 in FIG. 3, once the stent graft device 93 is deployed, the aneurysm 70 may not yet be isolated and additional stent graft leg extensions 12 may be deployed within the legs of the stent graft 93 as shown in FIG. 8. For some embodiments, an ipsilateral leg extension (not shown) and a contralateral leg extension 150 shown in FIG. 8 may be so deployed. Once one of the leg extensions 150 has been deployed with a proximal overlap section 50 thereof coupled and sealed to an inner surface of a leg, such as the contralateral leg 98 shown, of the bifurcated stent graft 93 and a distal seal section 52 coupled and sealed to an inner surface of an inner lumen of an iliac 151 artery as shown, it is time to deploy the second stent graft extension 12. The second stent graft extension 12 which is the last component of the modular stent graft system shown, is deployed with the delivery system 10 that includes the access conduit 36 as discussed above.

Figure 9:
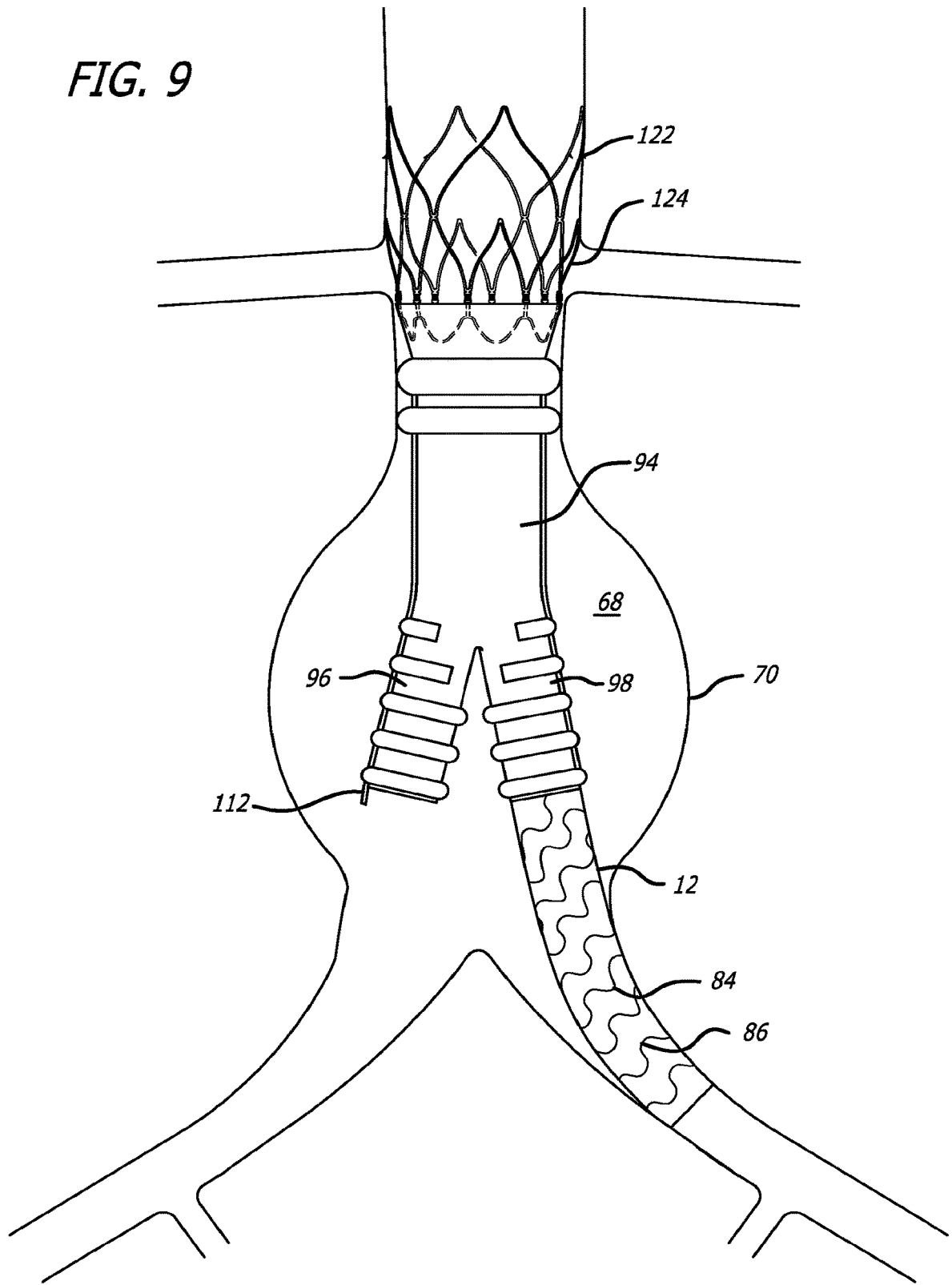
FIG. 9 illustrates the stent graft of FIG. 8 with the delivery catheter for the bifurcated stent graft withdrawn from the patient's vasculature.
Figure 10:
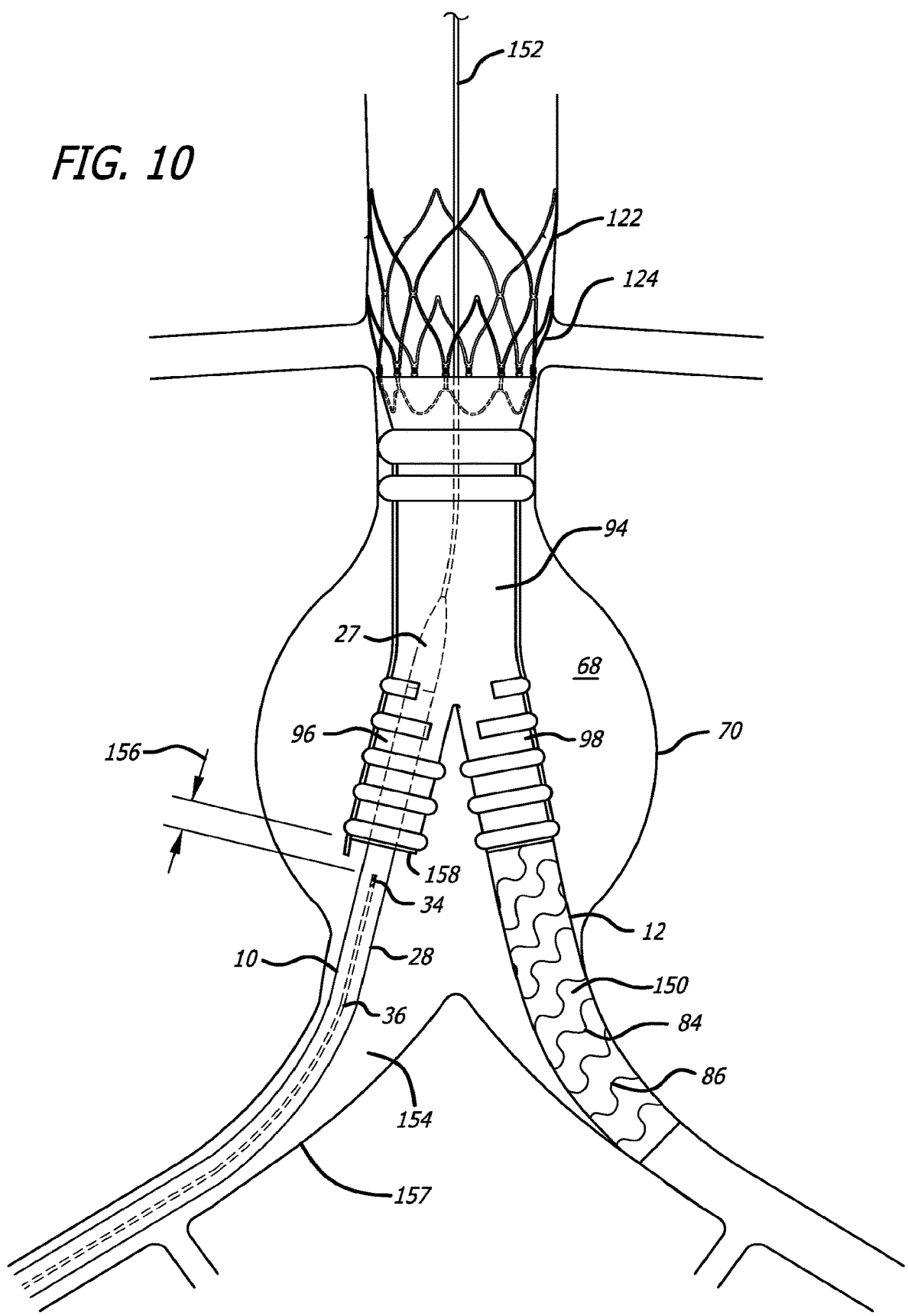
FIG. 10 shows the stent graft of FIG. in place with a distal portion of a stent graft delivery system for delivery of a stent graft extension disposed within an inner lumen of the ipsilateral leg of the bifurcated stent graft.
Figure 10A:
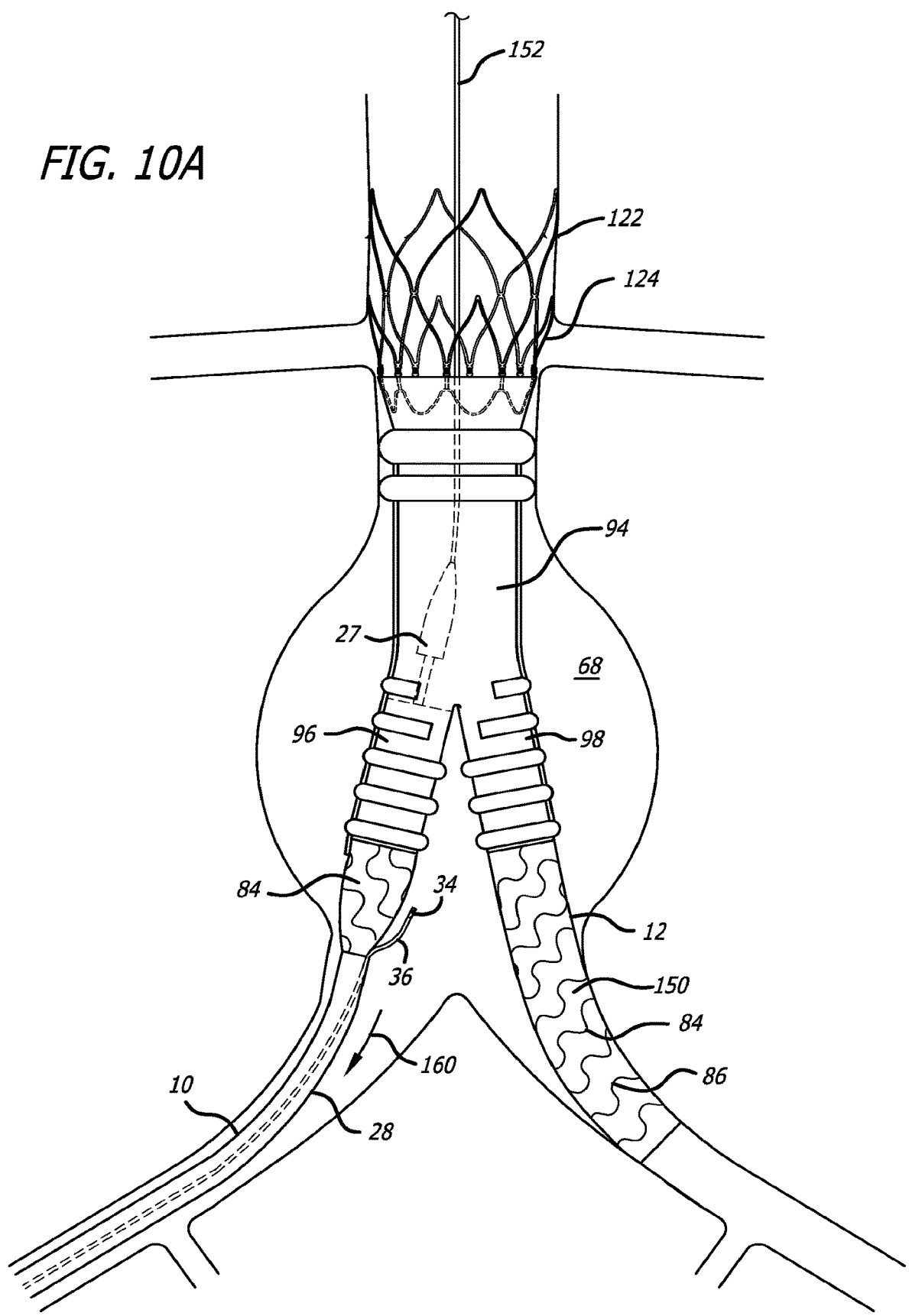
FIG. 10A shows the stent graft of the stent graft delivery system of FIG. 10 in a partially deployed state.
Figure 11:
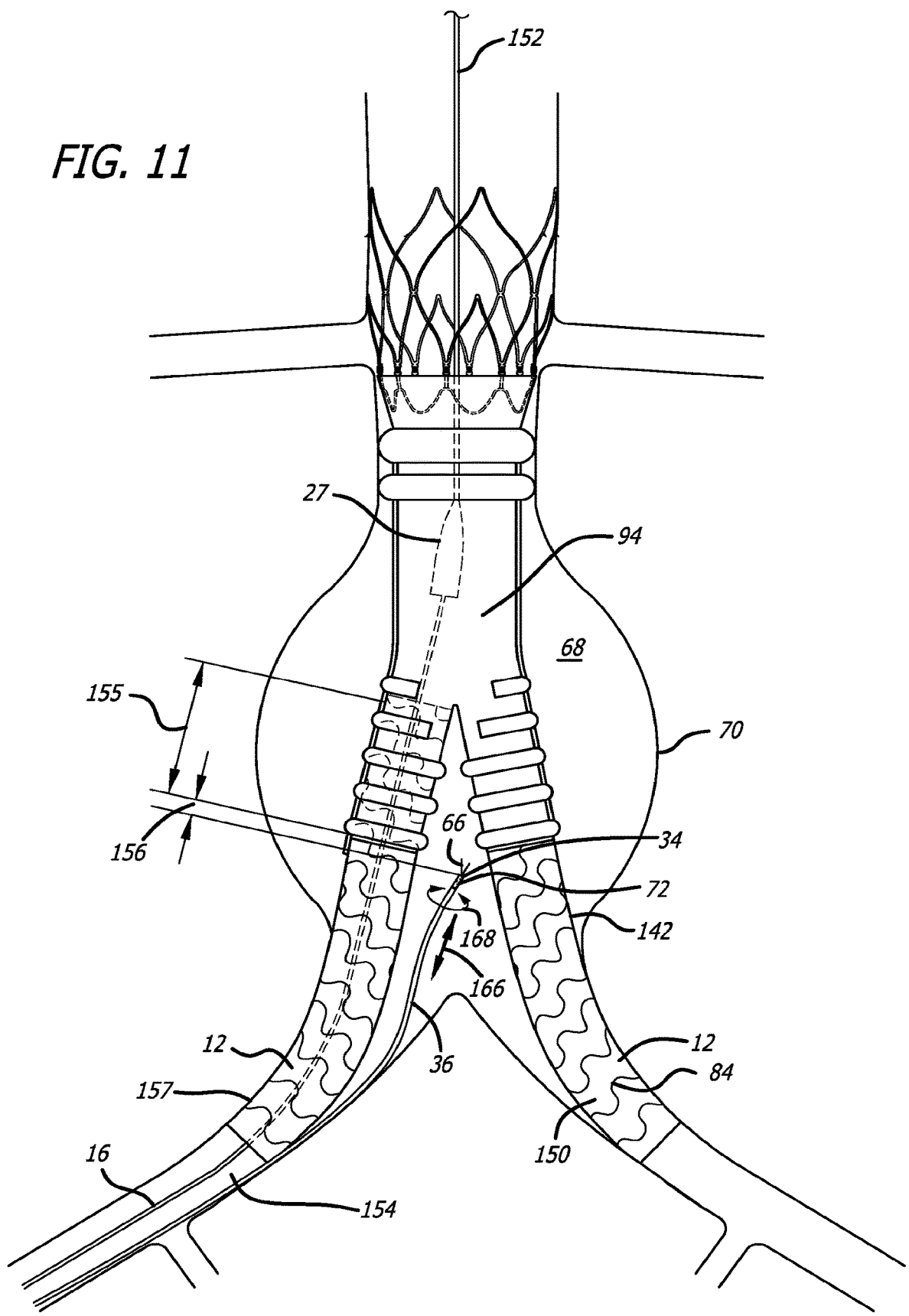
FIG. 11 illustrates a distal port of an aneurysm sac access conduit of the delivery system for the graft extension disposed in fluid communication with an interior volume of the aneurysm sac of FIG. 10.

Typically, before the last stent graft extension 12 is deployed, and particularly for cases wherein the stent graft extension 12 is being deployed in the same location as the delivery catheter 117, the delivery catheter 117 for the bifurcated endoluminal prosthesis/stent graft 93 is withdrawn from the patient's vasculature as shown on FIG. 9. Referring to FIGS. 10-11, some embodiments of a method for treating an enlarged portion of a patient's body vessel, such as the aneurysm 70, may include advancing the delivery system 10 over an optional guidewire 152 and through an inner lumen 154 of the patient's body vessel 157 as shown in FIG. 10. The delivery system 10 may include the stent graft 12 in a radially constrained state positioned relative to the delivery catheter 14 of the delivery system 10 such that the distal end 34 of the elongate tubular access conduit 36 of the delivery catheter 14 is disposed outside of the outer surface 32 of the stent graft 12. The distal end 34 of the access conduit 36 may be axially positioned between the distal end 74 of the proximal overlap section 50, which extends distally from the proximal end 120 of the stent graft 12, and the proximal end 76 of the distal seal section 52, which extends proximally from the distal end 46 of the stent graft 12 (as shown in FIG. 2). After so advancing the delivery system 10, at least a portion of the stent graft 12 may be deployed such that the proximal overlap section 50 of the stent graft 12 is coupled and sealed to an inner lumen, such as the inner lumen 102 of the ipsilateral leg 96 of the bifurcated endoluminal prosthesis 93 as shown in FIG. 10A. At this stage, the distal port 56 of the access conduit 36 is in fluid communication with the interior volume 68 of the enlarged portion of the patient's body vessel, or aneurysm 70, also as shown in FIG. 10A.

The delivery catheter 14 is generally distally advanced into a distal end 158 of a leg lumen 102 of the main graft body 94 as shown in FIG. 10 until the proximal overlap section 50 of the stent graft 12 overlaps the leg 96, as indicated by arrow 155, but a gap 156 remains in an axial direction between the distal end 34 of the access conduit 36 (as may be indicated and visualized by an operator by the radiopaque marker 72) and a distal end 158 of the leg 96 of the main graft body 94. Thereafter, the stent graft restraint such as the outer sheath 28 may be proximally retracted as shown by arrow 160 in FIG. 10A, and the stent graft 12 allowed to radially self-expand and be deployed partially within the inner lumen 102 of the leg of the stent graft 93. Proximally retracting the outer sheath 28 which is disposed about and radially constrains the stent graft 12 removes the outer radial constraint of an inner surface 30 of the outer sheath 28 from an outer surface 32 of the radially constrained stent graft 12. As a result, for the method embodiment shown, the stent graft 12 is partially deployed such that the proximal overlap section 50 is coupled and sealed to an inner surface of an inner lumen 102 of the leg 96 of the previously deployed bifurcated endoluminal prosthesis 93. Thereafter, the outer sheath 28 may be fully retracted in a proximal direction and the stent graft 12 thereby fully deployed with an outer surface of the distal seal section 52 of the stent graft 12 sealed to an inner surface of a lumen of a patient's vessel, such as the iliac artery 157 as shown in FIG. 11. Thus, after deployment of the stent graft 12, the access conduit 36 may be sandwiched between the stent graft device 12 and the iliac artery wall 157, with the distal port 56 at the distal end 34 of the access conduit 36 disposed in fluid communication with an interior volume 68 of the aneurysm sac 70 also as shown in FIG. 11.

At this point, completion angiography of the deployed AAA stent graft system, as well as injection of contrast media or the like into the aneurysm sac 68 through the inner lumen 60 of the access conduit 36 to assess if endoleaks are present, may be performed as needed. An arrow 162 is shown in FIG. 13A indicating a type 1 endoleak and an arrow 164 is shown indicating a type 2 endoleak resulting from blood flow reversal. Such endoleaks may be visualized under fluoroscopy imaging or the like after injection of contrast media or a combination of contrast media and saline solution in order to perform angiography of the interior volume 68 of the aneurysm 70 which is sometimes referred to as a "sacogram". In addition to determining whether endoleaks are present in the interior volume 68, such imaging techniques may also be used to determine whether or not it is appropriate to proceed with the injection of a thrombogenic material. For example, if a contrast media dissipates too quickly from the interior volume 68, injection of a thrombogenic material into the interior volume 68 may be contraindicated in some cases.

If appropriate to do so, a substance such as a thrombogenic material or other clinically useful material 66, as discussed above, may optionally be injected through the inner lumen 60 and out of the distal port 56 (or distal ports) of the access conduit 36 and into the interior volume 68 of the aneurysm sac 70 in response to any endoleaks thereby detected, or prophylactically even if no endoleaks are detected. Although a thrombogenic agent 66 such as Thrombin®, Floseal® or Fibrin® including Fibrin glue, may be used for injection into the interior volume 68 of the aneurysm 70, material for injection into the interior volume of the aneurysm may include these materials as well as Gelfoam®, contrast media, saline or any combination of these materials or any other suitable clinically useful materials may be injected into the interior volume 68 to promote thrombosis, facilitate imaging or any other suitable purpose. After injection of a thrombogenic material into the interior volume of the enlarged portion of the patient's vessel/aneurysm 70, a completion angiography of the deployed stent graft system may again be optionally performed.

In addition, once the access conduit 36 has been so deployed in fluid communication with the interior volume 68 of the aneurysm 70, some embodiments of the access conduit 36 may optionally be translated in an axial direction relative to an axial position of the elongate shaft 16 as shown by arrow 166 in FIG. 11. In addition, embodiments of the access conduit 36 may be rotated about the longitudinal axis 77 of the access conduit 36 relative to an angular position of the elongate shaft 16 as indicated by arrow 168 to use the optional preformed shaped distal end 34 of the access conduit 36 to be displaced and positioned in a controlled manner to access one or more desired positions within an interior volume 68 of the aneurysm 70. Thereafter, the delivery system 10 and associated access conduit 36 may be withdrawn from the patient's vessel while leaving the stent graft 12 in place in a deployed state that is at least partially relaxed and self-expanded.

Figure 12:
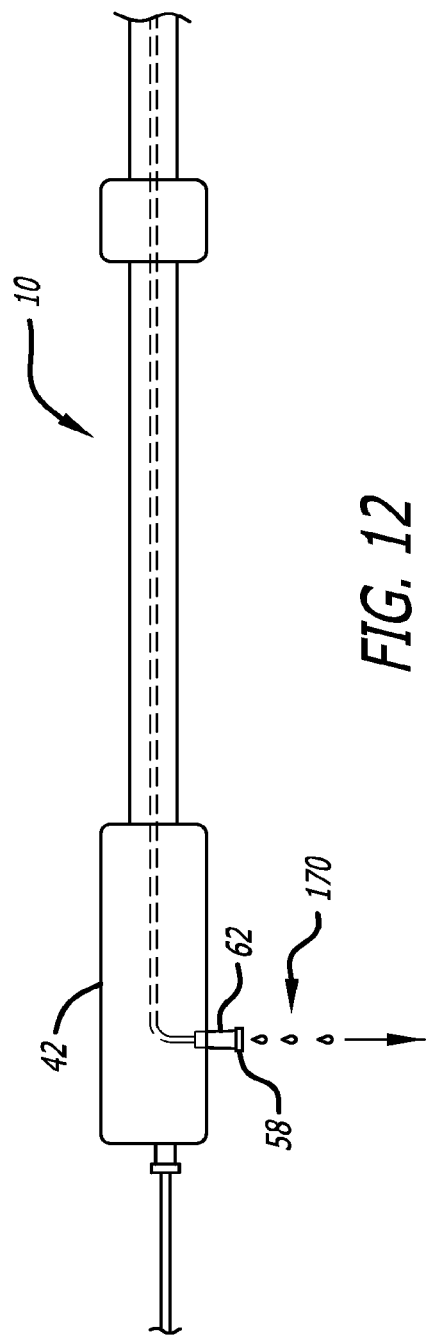
FIG. 12 is an elevation view of a proximal section of a delivery catheter embodiment showing blood leaking from a proximal port of an access conduit thereof.
Figure 13:
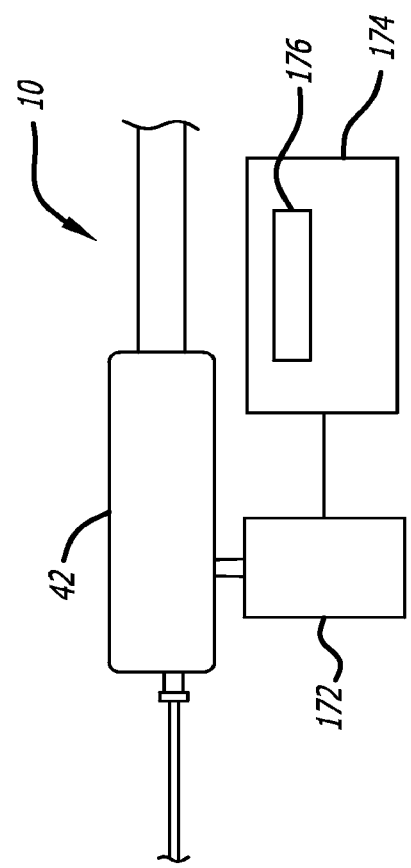
FIG. 13 is an elevation view of a proximal section of a delivery catheter embodiment with a flow meter and processor operatively coupled to a proximal port of an access conduit of the delivery catheter.
Figure 13A:
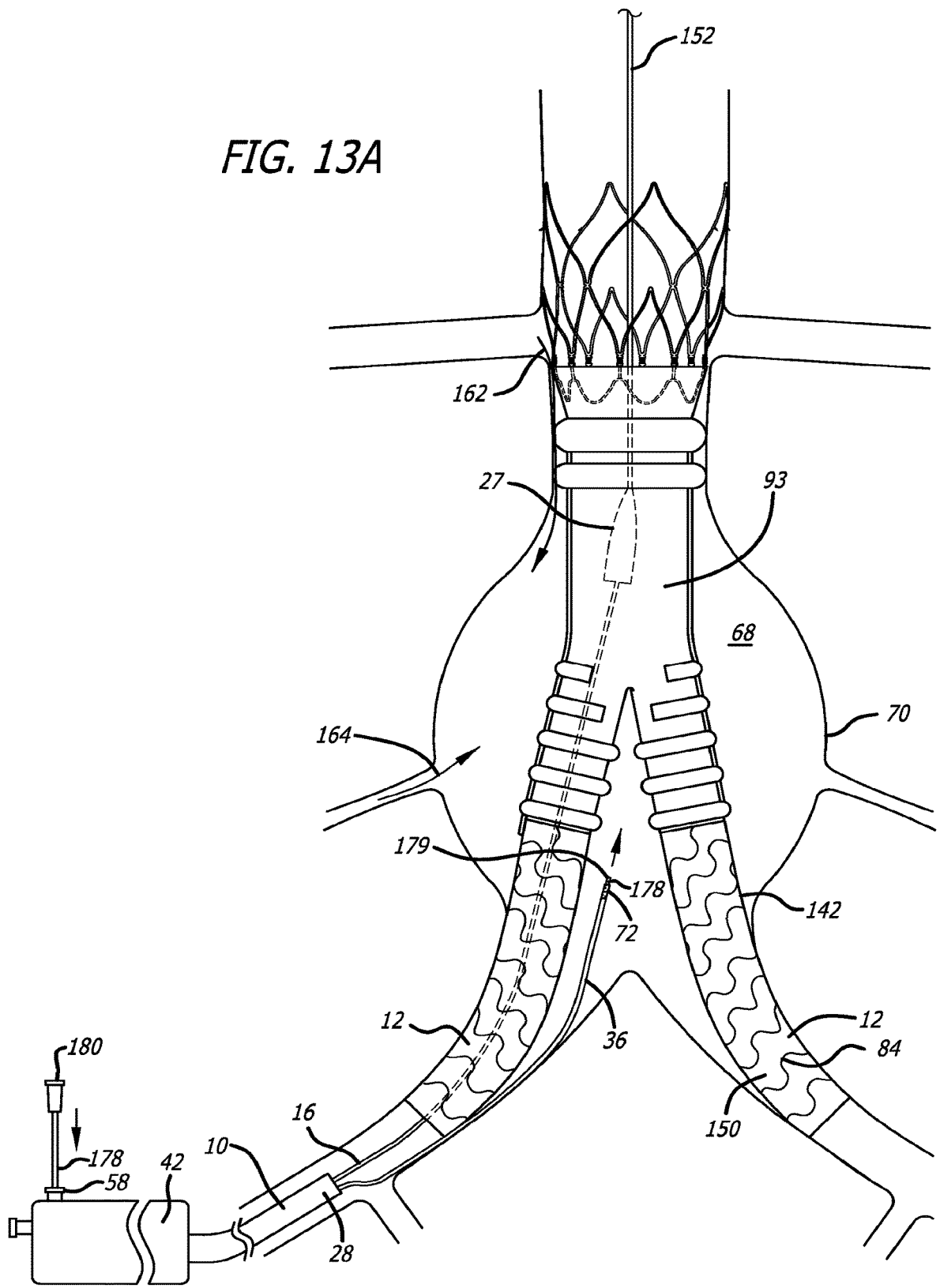
FIG. 13A shows a thick walled tubular member disposed within an inner lumen of the access conduit.

Referring to FIGS. 12 and 13, some embodiments of a method of detecting an endoleak during treatment of an aneurysm 70 of a patient may include advancing the delivery system 10 through the inner lumen of the artery of the patient to the aneurysm 70. In some cases, such a delivery system 10 may include the stent graft 12 in the radially constrained state positioned relative to the delivery catheter 14 of the delivery system 10 such that the distal end 34 of the elongate tubular access conduit 36 of the delivery catheter 14 is disposed outside of the outer surface 32 of the stent graft 12. The distal end 34 and optionally the distal port 56 of the access conduit 36 may also be axially positioned between the distal end 74 of the proximal overlap section 50, which extends distally from the proximal end 44 of the stent graft 12, and the proximal end 76 of the distal seal section 52, which extends proximally from the distal end 46 of the stent graft 12. Once the delivery system 10 has been so advanced, the stent graft 12 may be deployed such that the aneurysm 70 being treated is nominally isolated and fluidly sealed from the blood flow of the inner lumen of the artery 70 being treated. In addition, the stent graft 12 is deployed such that the distal port 56 of the access conduit 36 is in fluid communication with an interior volume 68 of the aneurysm 70. The method may further include establishing an open fluid pathway between the interior volume 68 of the aneurysm 70 and a position outside the patient's body using the inner lumen 60 of the access conduit 36 and detecting ongoing blood leakage 170 from the proximal port 58 of the inner lumen 60 of the access conduit 36. In some cases, detecting ongoing blood leakage 170 may include detecting ongoing blood leakage 170 using a meter mechanism 172 that may include an optional fluid flow meter, pressure sensor or any other suitable sensor or meter device. An optional fluid flowmeter 172 is shown coupled in fluid communication with the proximal port 58 of the access conduit 36 in FIG. 12.

With regard to such a endoleak detection method, in some cases an operator of the delivery system 10 may simply observe an ongoing flow of blood from the proximal port 58 of the access conduit 36 and make an assessment as to whether or not an endoleak is present based on the intensity and duration of blood flow from the proximal port 58. In other cases, detecting ongoing blood leakage 170 may include detecting ongoing blood leakage 170 using the optional fluid flowmeter 172 which is coupled in fluid communication with the proximal port 58 of the access conduit 36. A processor, control system or the like 174 may be operatively coupled to the fluid flowmeter 172 to measure flow intensity and duration. The processor 174 may be programmed or otherwise configured to make a determination regarding the presence of an endoleak based on the flow of blood from the proximal port 58 and display the results of the determination on a display screen 176 or by any other suitable mechanism such as an audible signal etc. In addition, if a pressure sensor is used as the meter device 172, the processor 174 may be programmed or otherwise configured to measure pressure within the interior volume 68 of the aneurysm and optionally compare this measured pressure to a reference pressure such as the patient's systolic blood pressure or any other suitable reference pressure. If the measured pressure within the interior volume 68 is sufficiently high in comparison to the reference pressure, then the presence of an endoleak may be confirmed.

As noted above, some embodiments of the access conduit 36 may include a thin walled configuration made from a soft supple material that will collapse due to external pressure in order to save space within the delivery catheter 14. For such embodiments, establishing an open fluid pathway between the interior volume 68 of the aneurysm 70 and a position outside the patient's body using the inner lumen 60 of the access conduit 36 may include distally advancing a relatively thick walled or substantially rigid tubular member 178 (or any other suitable catheter device) into the proximal port 58 of the access conduit 36, through the inner lumen 60 of the access conduit 36, out of the distal port 56 of the access conduit 36 and into the interior volume 68 of the aneurysm 70 as shown in FIG. 13A. As such, the open inner lumen 179 of the thick walled or substantially rigid tubular member 178 may provide the open fluid pathway between the interior volume 68 of the aneurysm 70 and a position outside the patient's body. A proximal port 180 of the thick walled tubular member 178 may then be operatively coupled to the optional fluid flow meter 172 or otherwise observed by an operator and monitored for ongoing blood leakage 170 from the proximal port 180. For such embodiments, the thick walled/substantially rigid tubular member 178 may be configured to maintain an open inner lumen 179 extending a length thereof even when an outside surface of the tubular member is exposed to external compression such as might be imposed by the self-expanding stent graft 12 against an artery wall. For such methods, the inner lumen 60 of the access conduit 36 may act as a guide or pathway for the tubular member that also has sufficient column strength to be forced through the inner lumen 60 of the collapsed access conduit 36. In some cases, once an endoleak is detected by any of the methods discussed herein, treatment such as injection of a thrombogenic material or any other suitable clinically useful material 66 into the interior volume 68 of the aneurysm 70 may then be performed.

Referring to FIG. 14, some embodiments of a kit 182 for treating a defect of a patient's body lumen, such as an aneurysm 70 in a patient's artery, may include the delivery system 10 for deployment of the stent graft 12 as discussed above. The kit 182 may further include a thrombogenic agent or other suitable clinically useful material 66 for delivery through the inner lumen 60 and from the distal port 56 of the access conduit 36. In some cases, such a thrombogenic agent 66 may be a liquid agent including materials such as Thrombin®, Fibrin®, Floseal®, Gelfoam®, contrast media, saline solution or the like. In some cases, the kit 182 may also include a vessel or container, such as a syringe 64, which includes an internal volume 186 to hold or otherwise contain the thrombogenic agent 66. Such an internal volume 186 of the syringe 64 is capable of being pressurized in order to inject the thrombogenic agent 66 through the inner lumen 60 of the access conduit 36 and into the interior volume 68 defect of the patient's body lumen, such as an aneurysm 70. The components of the kit 182 may be releasably secured to an optional base 188 that may be further packaged in an optional sterilizable container or the like (not shown).

As discussed above, the delivery system 10 device and method embodiments discussed herein may be particularly useful for endoluminal prosthesis embodiments which include one or more inflatable portions 106. Such inflatable endoluminal prosthesis embodiments 93 that may be deployed by the systems and methods discussed herein are discussed in U.S. Pat. No. 7,147,660 filed by M. Chobotov et al. on Dec. 20, 2002, titled "Advanced Endovascular Graft" which is hereby incorporated by reference herein in its entirety.

Delivery catheter embodiments discussed herein may include some or all of the features, dimensions or materials of delivery systems discussed in commonly owned U.S. Patent Application Publication No. 2004/0138734, published Jul. 15, 2004, filed Oct. 16, 2003, by Chobotov et al., titled "Delivery System and Method for Bifurcated Graft" and in PCT International Publication No. WO 02/083038, published Oct. 24, 2002, filed Apr. 11, 2001, by Chobotov et al., titled "Delivery System and Method for Bifurcated Graft" each of which is incorporated by reference herein in its entirety.

Endoluminal prosthesis embodiments discussed herein may include some or all of the features, dimensions or materials of the prostheses discussed in commonly owned U.S. Patent Publication No. 2009/0099649, filed Oct. 3, 2008, by Chobotov et al., titled Modular Vascular Graft for Low Profile Percutaneous Delivery, which is incorporated by reference herein in its entirety.

Examples of deployment devices, alignment devices, radiopaque markers delivery methods and the like that may be used in conjunction with any suitable system or component thereof discussed herein may be found in commonly owned U.S. Patent Application No. 2011/0218609, filed Feb. 9, 2011, by M. Chobotov et al., and titled "Fill Tube Manifold and Delivery Methods for Endovascular Graft", and U.S. Patent Publication No. 2013/0268048, filed Mar. 15, 2013, by J. Watson et al., and titled "Delivery Catheter for Endovascular Device", U.S. Patent Publication No. 2013/0268044, filed Mar. 13, 2013, by D. Parsons et al., and titled "Durable Stent Graft with Tapered Struts and Stable Delivery Methods and Devices", each of which is hereby incorporated by reference herein in its entirety.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the embodiments discussed. Although embodiments have been described in substantial detail with reference to one or more specific embodiments, those of ordinary skill in the art will recognize that changes may be made to the embodiments specifically disclosed in this application, yet these modifications and improvements are within the scope and spirit of the disclosure.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure. Certain embodiments of the technology are set forth in the claim(s) that follow(s).

What is claimed is:

1. A delivery system for deployment of a stent graft, comprising:
    a delivery catheter having an elongate tubular access conduit and an outer sheath; and
    a stent graft radially constrained by the outer sheath and positioned relative to the delivery catheter such that a distal end of the elongate tubular access conduit is disposed between an outer surface of the stent graft and an inner surface of the outer sheath,
    wherein the distal end of the access conduit is positioned between a distal end of a proximal overlap section, which extends distally from a proximal end of the stent graft, and a proximal end of a distal seal section, which extends proximally from a distal end of the stent graft, and
    wherein the proximal overlap section is configured to couple and seal an inner surface of an inner lumen of an endoluminal prosthesis, and
    wherein a distal port of the access conduit is configured to be in fluid communication with an interior volume of an enlarged portion of a patient's vessel,
    wherein the access conduit is disposed in an axially slidable relation relative to an elongate shaft of the delivery catheter such that an axial position of the distal end of the access conduit may be adjusted by adjusting an axial position of a proximal end of the access conduit relative to the elongate shaft.

2. The delivery system of claim 1, wherein the proximal overlap section of the stent graft includes an axial length of about 1 cm to 5 cm.

3. The delivery system of claim 1, wherein the distal seal section includes an axial length of about 1 cm to about 10 cm.

4. The delivery system of claim 1, wherein the access conduit is configured to rotate about a longitudinal axis thereof relative to an elongate shaft of the delivery catheter such that a circumferential position of the distal end of the access conduit may be adjusted by adjusting an axial position of a proximal end of the access conduit relative to an elongate shaft of the delivery catheter.

5. The delivery system of claim 1, wherein a distal section of the access conduit has a resilient preformed curved shape that may be used to position the distal port of the access conduit with the interior volume of the enlarged portion of the patient's vessel.

6. The delivery system of claim 1, wherein the endoluminal prosthesis includes an inflatable portion and an interior volume in fluid communication with an inflation port, and a proximal end of a fill tube of the delivery catheter releasably coupled to the inflation port.

7. The delivery system of claim 1, wherein the stent graft comprises a self-expanding stent graft.

8. The delivery system of claim 1, wherein the stent graft comprises an elongate tubular stent graft.

9. The delivery system of claim 1, wherein an elongate shaft of the delivery catheter comprises an elongate tubular guidewire lumen extending from a proximal end of the elongate shaft to a distal end of the elongate shaft.

10. The delivery system of claim 1, wherein the access conduit comprises a thin-walled flexible collapsible tube.

11. The delivery system of claim 10, wherein the access conduit comprises a nominal wall thickness of about 0.0005 inches to about 0.003 inches.

12. The delivery system of claim 10, wherein the tubular structure of the access conduit comprises expanded polytetrafluoroethylene (ePTFE).

13. The delivery system of claim 1, wherein the access conduit comprises a rigid self-supporting tube.

14. The delivery system of claim 1, wherein the access conduit further comprises a radiopaque marker disposed at the distal end of the access conduit.

15. A delivery system for deployment of a stent graft, comprising: a delivery catheter including: an elongate shaft having a proximal section and a distal section, a stent graft restraint that is configured to at least partially and releasably secure a stent graft in fixed relation to the elongate shaft, and an elongate tubular access conduit extending from the proximal section to the distal section of the elongate shaft, the access conduit further including a proximal end, a distal end, a distal port, a proximal port and an inner lumen extending between and in fluid communication with the distal port and proximal port; and a stent graft releasably secured to the distal section of the elongate shaft by the stent graft restraint with the stent graft in a radially constrained state, the stent graft comprising a proximal end, a distal end, and at least one inner lumen extending from the proximal end to the distal end, wherein the stent graft restraint comprises an axially slidable outer sheath disposed over the stent graft and elongate shaft with the outer sheath being configured to radially constrain the stent graft and with the distal end of the access conduit being disposed between an outer surface of the stent graft and an inner surface of the outer sheath when the outer sheath is disposed in a distal-most axial position, and wherein the distal end of the access conduit is positioned between the distal end of the stent graft, and the proximal end the stent graft.

16. The delivery system according to claim 15, wherein the stent graft comprises a proximal overlap section which extends distally from the proximal end of the stent graft and which has an axial length sufficient to couple and seal to an inner lumen, and a distal seal section which extends proximally from the distal end of the stent graft and which has an axial length sufficient to couple and seal to an inner surface of an inner lumen, and wherein the stent graft is positioned such that the distal end of the access conduit is axially positioned between a distal end of the proximal overlap section and a proximal end of the distal seal section of the stent graft.

17. The delivery system according to claim 16, wherein the proximal overlap section has an axial length sufficient to couple and seal to an inner surface of an inner lumen of an endoluminal prosthesis and the distal seal section has an axial length sufficient to couple and seal to an inner surface of a patient's vessel.

18. A system for treating an aneurysm, comprising:
a delivery system for deployment of a stent graft, comprising:
a delivery catheter including:
an elongate shaft having a proximal section and a distal section,
a stent graft restraint that is configured to at least partially and releasably secure a stent graft in fixed relation to the elongate shaft, and
an elongate tubular access conduit extending from the proximal section to the distal section of the elongate shaft, the access conduit further including a proximal end, a distal end, a distal port, a proximal port and an inner lumen extending between and in fluid communication with the distal port and proximal port; and
a stent graft releasably secured to the distal section of the elongate shaft by the stent graft restraint with the stent graft in a radially constrained state, the stent graft comprising a proximal end, a distal end, and at least one inner lumen extending from the proximal end to the distal end; and
a thrombogenic agent for delivery through the inner lumen and from the distal port of the access conduit,
wherein the stent graft restraint comprises an axially slidable outer sheath disposed over the stent graft and elongate shaft with the outer sheath being configured to radially constrain the stent graft and with the distal end of the access conduit being disposed between an outer surface of the stent graft and an inner surface of the outer sheath when the outer sheath is disposed in a distal-most axial position, and
wherein the distal end of the access conduit is positioned between the distal end of the stent graft, and the proximal end the stent graft.

19. The system of claim 18, wherein the thrombogenic agent comprises a liquid material.

* * * * *